United States Patent
Simone et al.

(10) Patent No.: US 7,632,425 B1
(45) Date of Patent: Dec. 15, 2009

(54) COMPOSITION AND ASSOCIATED METHOD

(75) Inventors: Davide Louis Simone, Gilboa, NY (US); Thomas Martin Angeliu, Clifton Park, NY (US); Jian Zhang, Schenectady, NY (US); Christopher Michael Carter, Gulfort, MS (US); David Alexander Gibson, III, Scotia, NY (US); Larry Neil Lewis, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 360 days.

(21) Appl. No.: 11/539,330

(22) Filed: Oct. 6, 2006

(51) Int. Cl.
- C09K 3/00 (2006.01)
- H01B 1/00 (2006.01)
- C22C 1/04 (2006.01)
- C21B 15/04 (2006.01)
- B22F 1/00 (2006.01)
- C08K 3/10 (2006.01)
- B32B 5/16 (2006.01)

(52) U.S. Cl. .......... 252/182.3; 252/500; 252/182.22; 252/182.26; 252/182.33; 252/182.34; 524/403; 428/323; 75/345; 75/10.1; 75/10.13; 977/810; 977/811

(58) Field of Classification Search .......... 252/182.3, 252/500, 182.22, 182.26, 182.33, 182.34; 524/403; 428/323; 75/345
See application file for complete search history.

(56) References Cited

U.S. PATENT DOCUMENTS

| | | | | |
|---|---|---|---|---|
| 3,706,592 A | * | 12/1972 | Thomson | 442/149 |
| 3,715,371 A | * | 2/1973 | Thomson | 534/558 |
| 4,400,326 A | * | 8/1983 | Daudt et al. | 556/10 |
| 4,496,754 A | * | 1/1985 | Kanner et al. | 556/420 |
| 5,759,230 A | * | 6/1998 | Chow et al. | 75/362 |
| 5,808,013 A | * | 9/1998 | Biagini et al. | 534/13 |
| 6,262,129 B1 | | 7/2001 | Murray et al. | |
| 6,673,954 B1 | * | 1/2004 | Gedon et al. | 556/420 |
| 6,721,083 B2 | | 4/2004 | Jacobson et al. | |
| 6,812,268 B2 | | 11/2004 | Schneider et al. | |
| 6,951,666 B2 | * | 10/2005 | Kodas et al. | 427/376.6 |
| 7,292,334 B1 | * | 11/2007 | Bratkovski et al. | 356/301 |
| 2003/0180451 A1 | | 9/2003 | Kodas et al. | |
| 2003/0218258 A1 | | 11/2003 | Charles et al. | |
| 2004/0079195 A1 | | 4/2004 | Perry et al. | |
| 2004/0242729 A1 | * | 12/2004 | Baran et al. | 523/200 |
| 2005/0008861 A1 | | 1/2005 | Yadav et al. | |
| 2005/0045855 A1 | * | 3/2005 | Tonapi et al. | 252/500 |

(Continued)

FOREIGN PATENT DOCUMENTS

DE    196 39 632 A1    4/1988

(Continued)

OTHER PUBLICATIONS

115393330 EIC STIC search results, pdf.*

(Continued)

*Primary Examiner*—Mark Eashoo
*Assistant Examiner*—Jane L Stanley
(74) *Attorney, Agent, or Firm*—Scott J. Asmus

(57) ABSTRACT

A composition includes a metal precursor. The metal precursor may include an inorganic ligand and a metal cation. The inorganic ligand may include a carbamate group. An associated method is provided.

20 Claims, 9 Drawing Sheets

U.S. PATENT DOCUMENTS

| | | | |
|---|---|---|---|
| 2005/0078158 A1 | 4/2005 | Magdassi et al. | |
| 2005/0113489 A1* | 5/2005 | Baran et al. | 523/300 |
| 2005/0175649 A1 | 8/2005 | Disalvo et al. | |
| 2006/0001726 A1 | 1/2006 | Kodas et al. | |
| 2006/0043346 A1* | 3/2006 | Kodas et al. | 252/514 |
| 2006/0065075 A1 | 3/2006 | Chang et al. | |
| 2006/0083694 A1 | 4/2006 | Kodas et al. | |
| 2006/0216438 A1* | 9/2006 | Nishimura et al. | 428/1.31 |
| 2007/0293611 A1* | 12/2007 | Ramanathan et al. | 524/176 |
| 2008/0083299 A1* | 4/2008 | Simone et al. | 75/345 |
| 2008/0085410 A1* | 4/2008 | Simone et al. | 428/355 CP |
| 2008/0085962 A1* | 4/2008 | Simone et al. | 524/403 |
| 2008/0118755 A1* | 5/2008 | Whiteford et al. | 428/403 |
| 2008/0206488 A1* | 8/2008 | Chung et al. | 427/596 |
| 2008/0268146 A1* | 10/2008 | Su et al. | 427/207.1 |

FOREIGN PATENT DOCUMENTS

| | | |
|---|---|---|
| WO | 2005054120 | 6/2005 |
| WO | 2005121222 | 12/2005 |
| WO | WO2005121222 A1 | 12/2005 |

OTHER PUBLICATIONS

"N,N-Dialkylcarbamato Complexes of the d Cations of Copper, Silver, and Gold", Alessio et al. Helvetica Chimica Acta, vol. 81 (1998), p. 219-230.*

Jong-Min Kim et al., "Isotropic Conductive Adhesives With Fusible Filler Particles", Journal of Electronic Materials, vol. 33, No. 11, pp. 1331-1337, 2004.

Kyoung-sik Moon et al., "Nano Metal Particles for Low Temperature Interconnect Technology", Electronic Components and Technology Conference, vol. 2, pp. 1983-1988, 2004.

Suresh Pothukuchi et al., "Shape Controlled Synthesis of Nanoparticles and Their Incorporation Into Polymers", Electronic Components and Technology Conference, vol. 2, pp. 1965-1967, 2004.

Lianhua Fan et al., "Electrical and Thermal Conductivities of Polymer Composites Containing Nano-Sized Particles", Electronic Components and Technology Conference, vol. 1, pp. 148-154, 2004.

Hai Dong et al., "Molecular Dynamics Study of Nanosilver Particles for Low-Temperature Lead-Free Interconnect Applications", Journal of Electronic Materials, vol. 34, No. 1, pp. 40-45, 2005.

Kyoung-sik Moon et al., "Thermal Behavior of Silver Nanoparticles for Low-Temperature Interconnect Applications", Journal of Electronic Materials, vol. 34, No. 2, pp. 168-175, 2005.

Lilei Ye et al., "Effect of Ag Particle Size on Electrical Conductivity of Isotropically Conductive Adhesives", IEEE Transactions on Electronics Packaging Manufacturing, vol. 22, No. 4, pp. 299-302, Oct. 1999.

Yi Li et al., "Improvement of Electrical Performance of Anisotropically Conductive Adhesives", IEEE Proceedings on Advanced Packaging Materials: Processes, Properties and Interfaces, pp. 221-226, 2005.

Hongjin Jiang et al., "The Role of Self-Assembled Monolayer (SAM) on Ag Nanoparticles for Conductive Nanocomposite", IEEE Proceedings on Advanced Packaging Materials: Processes, Properties and Interfaces, pp. 266-271, 2005.

Kimberly Dick et al., "Size-Dependent Melting of Silica-Encapsulated Gold Nanoparticles", Journal of American Chemical Society, vol. 124, No. 10, pp. 2312-2317, 2002.

Y. Fu et al., "Spatial Distribution of Metal Fillers in Isotropically Conductive Adhesives", Journal of Electronic Materials, vol. 30, No. 7, pp. 866-871, 2001.

Ph. Buffat et al., "Size Effect on the Melting Temperature of Gold Particles", Physical Review A, vol. 13, No. 6, pp. 2287-2298, Jun. 1976.

C. R. M. Wronski, "The Size Dependence of the Melting Point of Small Particles of Tin", British Journal of Applied Physics, vol. 18, pp. 1731-1737, 1967.

Hans-Gerd Busmann et al., "Polymer Matrix Composites Filled With Nanoporous Metal Powders: Preparation and Electrical Properties", NanoStructured Materials, vol. 12, pp. 531-534, 1999.

W. Fritzsche et al., "In-Situ Formation of Ag-Containing Nanoparticles in Thin Polymer Films", Nanostructured Materials, vol. 10, No. 1, pp. 89-97, 1998.

Zhongping Zhang et al., "A Convenient Route to Polyacrylonitrile/Silver Nanoparticle Composite by Simultaneous Polymerization-Reduction Approach", Polymer Communication, vol. 42, pp. 8315-8318, 2004.

Jongnam Park et al., "Ultra-Large-Scale Syntheses of Monodisperse Nanocrystals", Nature Materials, vol. 3, pp. 891-895, 2004.

Yu Lu et al., "High-Density Silver Nanoparticle Film With Temperature-Controllable Interparticle Spacing for a TUnable Surface Enhanced Raman Scattering Substrate", American Chemical Society, Nano Letters, vol. 5, No. 1, pp. 5-9, 2005.

Sihai Chen et al., "A Novel Method for Large-Scale Synthesis of AgI Nanoparticles", Chemical Communications, pp. 2301-2302, 1997.

Lugi Abis et al., "N,N-Dialkylcarbamato Complexes as Precursors for the Chemical Implantation of Metal Cations on a Silica Support Part 2.-Platinum (II) and Its Further Reduction to Platinum Nanopartilces", Journal of Materials Chemistry, vol. 8, No. 3, pp. 751-759, 1998.

Nikhil R. Jana et al., "Wet Chemical Synthesis of Silver Nanorods and Nanowires of Controllable Aspect Ratio", Chemical Communications, pp. 617-618, 2001.

Rocco Alessio et al., "N,N-Dialkylcarbamato Complexes of Silver (*)(**)" Gazzetta Chimica Italiana, vol. 123, pp. 719-721, 1993.

* cited by examiner

COMPOSITION AND ASSOCIATED METHOD

BACKGROUND

1. Technical Field

The invention includes embodiments that relate to a composition. The invention includes embodiments that relate to method of making and using the composition.

2. Discussion of Related Art

Nano-scale metal particles (nanoparticles) may have properties different from those of bulk metal or atomic species. Differences in properties may be due in part because of the large surface area of the metal nanoparticles, electronic structure differences, higher percentage of surface atoms, or differences in melting, freezing and diffusion behavior of metal nanoparticles. Nanoparticles and compositions with nanoparticles may find applications in diverse fields, for example, in microelectronics, optical, electrical, and magnetic devices, sensors, electrochemistry, catalytic applications.

Metal nanoparticles may be used in one of the aforementioned applications alone or with polymer matrices. A method of forming the nanoparticles may include reducing a metal salt (metal precursor), for example, a silver carboxylate using a suitable reducing agent. Carboxylate and other similar salts of metals may necessitate heating the metal salt to temperatures greater than 200 degrees Celsius. High temperatures and violent nature of the reduction reaction may not be amenable in applications where low processing temperatures may be required. For example, such high reduction temperatures may not be suitable for polymer matrices that may cure, melt, or degrade at these temperatures. Nanoparticles may also show propensity towards associate formation, which in certain applications may necessitate incorporation of additional materials, for example, surfactants to facilitate dispersion of the metal nanoparticles, for example, in a polymer matrix.

Metal particles dispersed in a suitable polymer matrix may find applications as conductive adhesives. Conductive adhesives may be used as lead-free solders, thermal interface materials, and the like in electronic packaging applications. Conductive (electrical or thermal) properties of the adhesives may be limited in part because of interface resistance between particles. Higher particle concentrations may be required to achieve the desired conductive properties, which may affect the adhesive processability and also adhesion.

It may be desirable to have a metal precursor with properties that differs from those properties of currently available metal precursors. It may be desirable to have a metal nanoparticle with properties that differ from those properties of currently available metal nanoparticles. It may be desirable to have conductive adhesives with properties that differ from those properties of currently available conductive adhesives. It may be desirable to have a metal nanoparticle produced by a method that differs from those methods currently available. It may be desirable to have a conductive adhesive produced by a method that differs from those methods currently available.

BRIEF DESCRIPTION

In one embodiment, a composition is provided. The composition includes a metal precursor. The metal precursor includes an inorganic ligand and a metal cation. The inorganic ligand includes a carbamate group.

In one embodiment, a method is provided. The method includes heating a metal precursor to a reaction temperature and forming a decomposition product. The metal precursor includes a carbamate and a metal cation. The decomposition product includes a metal nanoparticle.

In one embodiment, a composition is provided. The composition includes a metal precursor. The metal precursor includes a carbamate-containing inorganic ligand and a metal cation. The metal precursor is responsive to a stimulus to form a metal nanoparticle.

BRIEF DESCRIPTION OF DRAWING FIGURES

DETAILED DESCRIPTION

Figure 1:
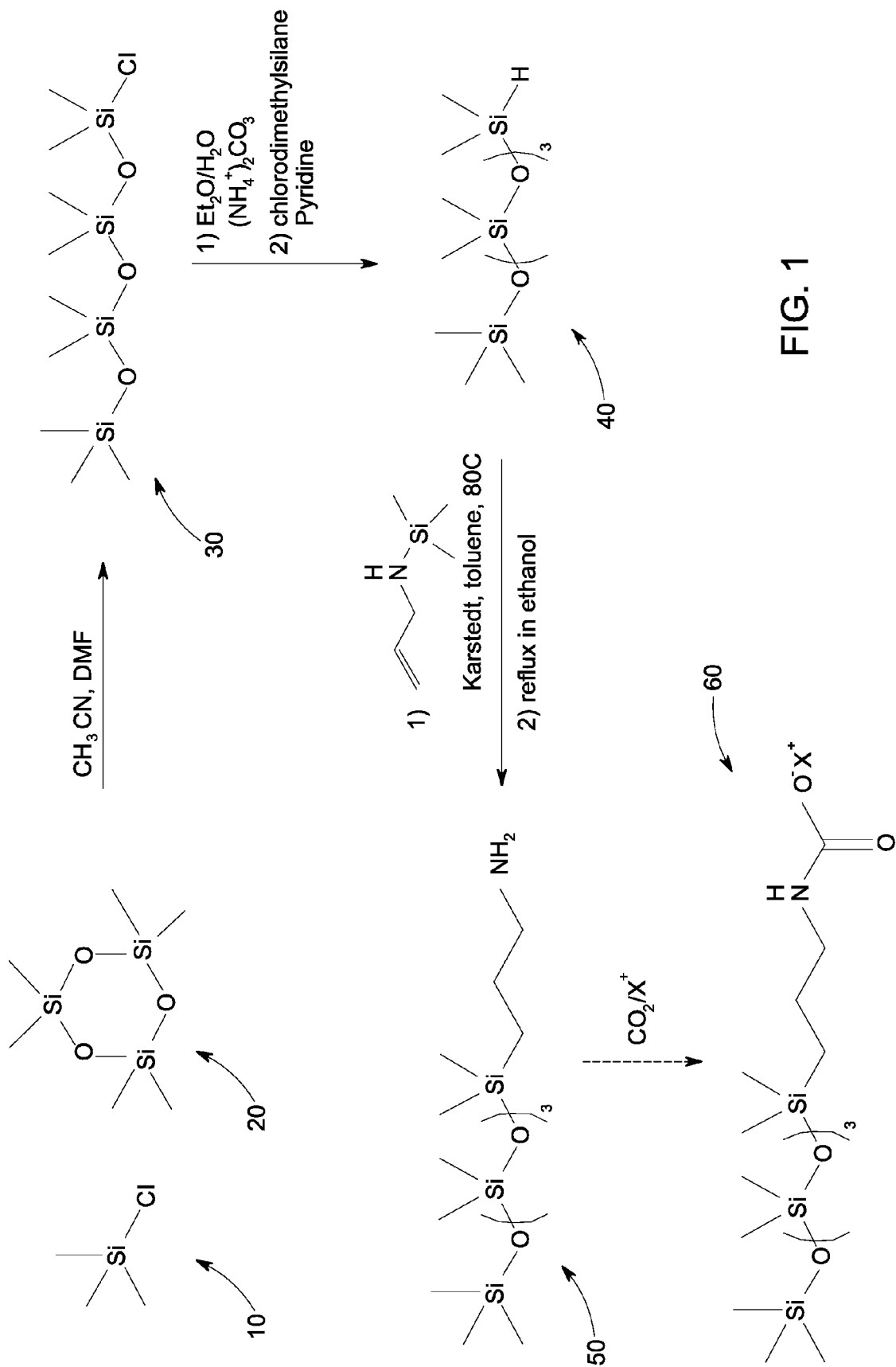
FIG. 1 is a reaction scheme comprising an embodiment of the invention for the synthesis of a metal precursor.

In the following specification and the claims which follow, reference will be made to a number of terms have the following meanings. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not limited to the precise value specified. In some instances, the approximating language may correspond to the precision of an instrument for measuring the value. Similarly, "free" may be used in combination with a term, and may include an insubstantial number, or trace amounts, while still being considered free of the modified term. For example, free of solvent or solvent-free, and like terms and phrases, may refer to an instance in which a significant portion, some, or all of the solvent has been removed from a solvated material.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be".

A composition according to an embodiment of the invention includes a decomposition product of a metal precursor. A metal precursor refers to a metal-containing compound capable of converting to an elemental metal when exposed to a stimulus. Elemental metal refers to a substantially pure metal or alloy having an oxidation state of zero. A metal precursor may include a ligand and one or more metals. Suitable metals may include one or more metal oxides, or mixed metal oxides. In one embodiment, the metal may include one or more silver (Ag), copper (Cu), or zinc (Zn). In one embodiment, the metal may include one or more magnetic metals. In one embodiment, the metal oxide may include one or more of silver (Ag), copper (Cu), or zinc (Zn). In one embodiment, the metal consists only of silver.

A suitable ligand may include a molecule or an ion having at least one atom having a lone pair of electrons that may bond to a metal atom or ion. A ligand may also include unsaturated molecules or ions that may bind to a metal atom or ion. Unsaturated molecules or ions may include at least one carbon-carbon double bond formed by the side-by-side overlap of p-atomic orbitals on adjacent atoms. In one embodiment, the ligand includes at least one carbamate group. A carbamate group may bind to metal atom or an ion through an oxygen anion in the carbamate group.

The ligand may have one or both of an organic backbone or an inorganic backbone. An organic backbone for the ligand may have only carbon-carbon linkages (for example, olefins) or carbon-heteroatom-carbon linkages (for example, ethers, esters and the like) in the main chain. An inorganic backbone for a ligand may include main chain linkages other than that of carbon-carbon linkages or carbon-heteroatom-carbon linkages, for example, silicon-silicon linkages in silanes, silicon-oxygen-silicon linkages in siloxanes, phosphorous-nitrogen-phosphorous linkages in phosphazenes, and the like.

In one embodiment, a ligand may include a structure of formula (I):

(I)

wherein "n" is 1 or 2, $X^+$ is a metal cation, and $R^1$ includes an aliphatic radical, a cycloaliphatic radical, an aromatic radical, or a silicon-containing group. Aliphatic radical, aromatic radical and cycloaliphatic radical may be defined as follows:

An aliphatic radical is an organic radical having at least one carbon atom, a valence of at least one and may be a linear or branched bonded array of atoms. Aliphatic radicals may include heteroatoms such as nitrogen, sulfur, silicon, selenium and oxygen or may be composed exclusively of carbon and hydrogen. Aliphatic radical may include a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example, carboxylic acid derivatives such as esters and amides), amine groups, nitro groups and the like. For example, the 4-methylpent-1-yl radical is a $C_6$ aliphatic radical comprising a methyl group, the methyl group being a functional group, which is an alkyl group. Similarly, the 4-nitrobut-1-yl group is a $C_4$ aliphatic radical comprising a nitro group, the nitro group being a functional group. An aliphatic radical may be a haloalkyl group that includes one or more halogen atoms, which may be the same or different. Halogen atoms include, for example; fluorine, chlorine, bromine, and iodine. Aliphatic radicals having one or more halogen atoms include the alkyl halides: trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g., —$CH_2CHBrCH_2$—), and the like. Further examples of aliphatic radicals include allyl, aminocarbonyl (—$CONH_2$), carbonyl, dicyanoisopropylidene —$CH_2C(CN)_2CH_2$—), methyl (—$CH_3$), methylene (—$CH_2$—), ethyl, ethylene, formyl (—CHO), hexyl, hexamethylene, hydroxymethyl (—$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$), thiocarbonyl, trimethylsilyl (($CH_3)_3Si$—), t-butyldimethylsilyl, trimethoxysilylpropyl (($CH_3O)_3SiCH_2CH_2CH_2$—), vinyl, vinylidene, and the like. By way of further example, a "$C_1$-$C_{30}$ aliphatic radical" contains at least one but no more than 30 carbon atoms. A methyl group ($CH_3$—) is an example of a $C_1$ aliphatic radical. A decyl group ($CH_3(CH_2)_9$—) is an example of a $C_{10}$ aliphatic radical.

An aromatic radical is a bonded array of atoms having a valence of at least one and having at least one aromatic group. This bonded array may include heteroatoms such as nitrogen, sulfur, selenium, silicon and oxygen, or may be composed exclusively of carbon and hydrogen. Suitable aromatic radicals may include phenyl, pyridyl, furanyl, thienyl, naphthyl, phenylene, and biphenyl radicals. The aromatic group may be a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical also may include non-aromatic components. For example, a benzyl group may be an aromatic radical, which includes a phenyl ring (the aromatic group) and a methylene group (the non-aromatic component). Similarly a tetrahydronaphthyl radical is an aromatic radical comprising an aromatic group ($C_6H_3$) fused to a non-aromatic component —($CH_2)_4$—. An aromatic radical may include one or more functional groups, such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group, which is an alkyl group. Similarly, the 2-nitrophenyl group is a C6 aromatic radical comprising a nitro group, the nitro group being a functional group. Aromatic radicals include halogenated aromatic radicals such as trifluoromethylphenyl, hexafluoroisopropylidenebis (4-phen-1-yloxy) (—$OPhC(CF_3)_2PhO$—), chloromethylphenyl, 3-trifluorovinyl-2-thienyl, 3-trichloromethyl phen-1-yl (3-$CCl_3Ph$—), 4-(3-bromoprop-1-yl) phen-1-yl ($BrCH_2CH_2CH_2Ph$—), and the like. Further examples of aromatic radicals include 4-allyloxyphen-1-oxy, 4-aminophen-1-yl ($H_2NPh$—), 3-aminocarbonylphen-1-yl ($NH_2COPh$—), 4-benzoylphen-1-yl, dicyanoisopropylidenebis(4-phen-1-yloxy) (—$OPhC(CN)_2PhO$—), 3-methylphen-1-yl, methylene bis(phen-4-yloxy) (—$OPhCH_2PhO$—), 2-ethylphen-1-yl, phenylethenyl, 3-formyl-2-thienyl, 2-hexyl-5-furanyl; hexamethylene-1,6-bis(phen-4-yloxy) (—$OPh(CH_2)_6PhO$—), 4-hydroxymethyl phen-1-yl (4-$HOCH_2Ph$—), 4-mercaptomethyl phen-1-yl (4-$HSCH_2Ph$—), 4-methylthio phen-1-yl (4-$CH_3SPh$—), 3-methoxy phen-1-yl, 2-methoxycarbonyl phen-1-yloxy (e.g., methyl salicyl), 2-nitromethyl phen-1-yl (—$PhCH_2NO_2$), 3-trimethylsilylphen-1-yl, 4-t-butyldimethylsilylphenl-1-yl, 4-vinylphen-1-yl, vinylidenebis(phenyl), and the like. The term "a $C_3$-$C_{30}$ aromatic radical" includes aromatic radicals containing at least three but no more than 30 carbon atoms. The aromatic radical 1-imidazolyl ($C_3H_2N_2$—) represents a $C_3$ aromatic radical. The benzyl radical ($C_7H_7$—) represents a $C_7$ aromatic radical.

A cycloaliphatic radical is a bonded array of atoms including a radical having a valence of one or more, and the bonded array including at least one portion that is cyclic but is not aromatic. A cycloaliphatic radical may include one or more non-cyclic components. For example, a cyclohexylmethyl group ($C_6H_{11}CH_2$—) is a cycloaliphatic radical, which includes a cyclohexyl ring (the array of atoms, which is cyclic but which is not aromatic) and a methylene group (the non-cyclic component). The cycloaliphatic radical may include heteroatoms such as nitrogen, sulfur, selenium, silicon and oxygen, or may be composed exclusively of carbon and hydrogen. A cycloaliphatic radical may include one or more functional groups, such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group, which is an alkyl group. Similarly, the 2-nitrocyclobut-1-yl radical is a $C_4$ cycloaliphatic radical comprising a nitro group, the nitro group being a functional group. A cycloaliphatic radical may include one or more halogen atoms, which may be the same or different. Halogen atoms include, for example, fluorine, chlorine, bromine, and iodine. Cycloaliphatic radicals having one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene 2,2-bis(cyclohex-4-yl) (—$C_6H_{10}C(CF_3)_2C_6H_{10}$), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}$—), and the like. Further examples of cycloaliphatic radicals include 4-allyloxycyclohex-1-yl, 4-aminocyclohex-1-yl ($H_2C_6H_{10}$), 4-aminocarbonylcyclopent-1-yl ($NH_2COC_5H_8$—), 4-acetyloxycyclohex-1-yl, 2,2-dicyanoisopropylidenebis(cyclohex-4-yloxy) (—$OC_6H_{10}C(CN)_2C_6H_{10}O$—), 3-methylcyclohex-1-yl, methylenebis(cyclohex-4-yloxy) (—$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy)(—$OC_6H_{10}(CH_2)_6 C_6H_{10}O$—); 4-hydroxymethylcyclohex-1-yl (4-$HOCH_2C_6H_{10}$—), 4-mercaptomethylcyclohex-1-yl (4-$HSCH_2C_6H_{10}$—), 4-methylthiocyclohex-1-yl (4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl ($NO_2CH_2C_6H_{10}$—), 3-trimethylsilylcyclohex-1-yl, 2-t-butyldimethylsilylcyclopent-1-yl, 4-trimethoxysilylethylcyclohex-1-yl (e.g. ($CH_3O)_3SiCH_2CH_2C_6H_{10}$—), 4-vinylcyclohexen-1-yl, vinylidenebis(cyclohexyl), and the like. The term "a $C_3$-$C_{30}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

In one embodiment, $R^1$ may be an aliphatic radical having one or more carbon atoms. In one embodiment, $R^1$ may be an aliphatic radical having carbon atoms in a range of from 1 to about 10, from about 10 to about 20, from about 20 to about 50, or from about 50 to about 100. In one embodiment, $R^1$ may be selected from the group consisting of a methyl radical, an ethyl radical, a propyl radical, a butyl radical, a pentyl radical, a hexyl radical, a heptyl radical, an octyl radical, a nonyl radical, and a decyl radical. In one embodiment, $R^1$ consists essentially of an aliphatic radical having 7 or more carbon atoms.

In one embodiment $X^{+n}$ may include a silver cation ($Ag^+$). In another embodiment, $X^{+n}$ consists essentially of silver cation ($Ag^+$), and is free of any other metal.

In one embodiment, $R^1$ may include silicon-silicon linkages such as in silanes. Silanes may also be referred to as organosilanes, where organosilanes include silicon-silicon linkages and one or more silicon atoms is substituted with an organic group. In one embodiment $R^1$ may include silicon-nitrogen-silicon linkages such as in silazanes. Silazanes include the organosilazanes that have silicon-nitrogen-silicon linkages and one or more silicon atoms are substituted with an organic group. $R^1$ may include silicon-oxygen-silicon linkages, such as in siloxanes. Siloxanes include the organosiloxanes that have silicon-oxygen-silicon linkages and one or more of the silicon atoms are substituted with an organic group. Suitable siloxanes may include linear siloxanes, cyclic siloxanes, branched siloxanes, partially crosslinked siloxanes, or silsesquioxanes.

In one embodiment, $R^1$ includes a structure of formula (II):

$$M_aD_bT_cQ_dR^2 \quad (II)$$

wherein the subscripts "a", "b", "c", and "d" are independently zero or a positive integer, and the sum of integers "a", "b", "c", and "d" is greater than or equal to 1, and M has the formula:

$$R^3R^4R^5SiO_{1/2}, \quad (III)$$

D has the formula:

$$R^6R^7SiO_{2/2}, \quad (IV)$$

T has the formula:

$$R^8SiO_{3/2}, \quad (V)$$

and Q has the formula:

$$SiO_{4/2}, \quad (VI)$$

and $R^2$ is a divalent radical having formula $$-Si(R^9)(R^{10})-CH_2-CH(R^{11})(R^{12})_z-, \quad (VII)$$

wherein $R^3$ to $R^{10}$ are independently an aliphatic radical, a radical, or an aromatic radical; $R^{11}$ is a hydrogen atom or an aliphatic radical; $R^{12}$ is a divalent aliphatic radical, and "z" is 0 or 1.

In one embodiment, $R^1$ includes a linear organosiloxane having a structure of formula (VIII):

$$MD_bR^2 \quad (VIII)$$

"b", M, D and $R^2$ are as defined hereinabove. The value of "b" may determine the molecular weight of the metal precursor and the physical properties of the metal precursor. In one embodiment, "b" may be 0. In one embodiment, "b" may be in a range of from 1 to about 10, from about 10 to about 50, or from about 50 to about 100. In one embodiment, "b" may be in a range of greater than about 10. In one embodiment, $R^2$ consists essentially of a linear polydimethysiloxane.

Suitability of a ligand for the metal precursor may be determined by one or more of physical properties of the metal precursor (for example stability of the ligand at room temperature), stimulus required to decompose the metal precursor (for example temperature), amount of metal in the metal precursor, compatibility of the metal precursor with additional materials (for example polymers, oligomers, and the like), or end use application of the decomposition product.

In one embodiment, the metal precursor may be stable to light at room temperature. In one embodiment, the metal precursor may be stable to moisture at room temperature. Stability, as used herein in the specification and claims, refers to the ratio of molecular weight of the metal precursor before exposure to light or moisture and after exposure to light or moisture.

The amount of metal precursor in the composition may vary depend on one or more of: the end-use, relative amount of metal in the entire metal precursor, amount of metal required in the final composition, and other factors. In one embodiment, the composition may include a metal precursor present in an amount that is less than about 0.1 weight percent. In one embodiment, the composition may include a metal precursor present in an amount in a range of from about 0.1 weight percent to 1 weight percent, from 1 weight percent to about 2 weight percent, from about 2 weight percent to about 5 weight percent, from about 5 weight percent to about 10 weight percent of the composition. In one embodiment, the composition may include a metal precursor present in an amount in a range of from about 10 weight percent to about 20 weight percent, from about 20 weight percent to about 30 weight percent, from about 30 weight percent to about 40 weight percent, or from about 40 weight percent to about 50 weight percent of the composition. In one embodiment, the composition may include a metal precursor present in an amount that is greater than about 50 weight percent.

In one embodiment, the metal precursor may decompose when exposed to a first stimulus that is either electromagnetic radiation or thermal energy. Electromagnetic radiation may include ultraviolet, visible, electron beam, or microwave radiation. Electromagnetic radiation may include a coherent beam, for example, in a laser. Thermal energy may include infra-red or the application of heat to the metal precursor resulting in an increase in temperature of the composition. In one embodiment, the metal precursor may decompose by heating the metal precursor to a temperature in a range of from about room temperature (RT) to about 40 degrees Celsius, from about 40 degrees Celsius to about 60 degrees Celsius, from about 60 degrees Celsius to about 80 degrees Celsius, from about 80 degrees Celsius to about 100 degrees Celsius, from about 100 degrees Celsius to about 120 degrees Celsius, or from about 120 degrees Celsius to about 150 degrees Celsius. In one embodiment, the metal precursor may decompose by heating the metal precursor to a temperature in a range of from about 150 degrees Celsius to about 175 degrees Celsius to, from about 175 degrees Celsius to about 200 degrees Celsius, from about 200 degrees Celsius to about 225 degrees Celsius, or from about 225 degrees Celsius to about 250 degrees Celsius. In one embodiment, the metal precursor may decompose only at a temperature that is less than about 120 degrees Celsius.

In one embodiment, two or more metal precursors may be used in the composition to form metal alloys and/or metal compounds. To form alloys, the two (or more) metal precursors may have similar decomposition temperatures to avoid the formation of one of the metal species before the other species. In one embodiment, the decomposition temperatures of the different metal precursors may by within about 50 degrees Celsius, within about 25 degrees Celsius, within about 10 degrees Celsius, or within about 5 degrees Celsius of each other.

In one embodiment, the first stimulus may include contact with a reducing agent. A reducing agent is a compound capable of reducing the metal cation in the metal precursor to its elemental form. In one embodiment, the reducing agent may be selected from the group consisting of alcohols, aldehydes, amines, amides, alanes, boranes, borohydrides, aluminohydrides, onium salts, and organosilanes. In one embodiment, the reducing agent consists only of one or more of onium salt, alcohol, amine, amide, borane, borohydride, or organosilane. In one embodiment, the reducing agent consists only of an onium salt. In one embodiment, the reducing agent consists only of an iodonium salt. In one embodiment, the first stimulus may include application of thermal energy and contact with a reducing agent.

The amount of reducing agent in the composition may depend on the reaction conditions and on the selected metal precursor. In one embodiment, the reducing agent may be present in an amount equal to or greater than the minimum stoichiometric amount necessary to convert all of the metal in the metal precursor to its elemental form at the desired conversion conditions. In one embodiment, an amount of primary reducing agent in the composition may be in excess relative to the amount of metal precursor to be converted to elemental form.

In one embodiment, a decomposition product of the metal precursor may include a metal nanoparticle. Nanoparticle as used herein, may refer to a single nanoparticle, a plurality of nanoparticles, or a plurality of nanoparticles associated with each other. Associated refers to a metal nanoparticle in contact with at least one other metal nanoparticle. In one embodiment, associated refers to a metal nanoparticle in contact with more than one other particle.

A decomposition product of the metal precursor may also include a decomposition product of the ligand. In one embodiment, a decomposition product of the metal precursor may include carbon dioxide and an amine. An amine may have a structure of formula $R^1NH_2$, wherein $R^1$ is as defined hereinabove in formula (I). In one embodiment, a composition may include a metal nanoparticle, an amine having formula $R^1NH_2$, and carbon dioxide. In one embodiment, metal precursors may include ligands that eliminate cleanly upon decomposition and escape completely from the composition. These metal precursors may not be susceptible to carbon contamination or contamination by anionic species (such as nitrates). In one embodiment, carbon dioxide may be released from the composition during or after the decomposition reaction and the composition may be free of carbon dioxide.

An amine may be dispersed in the composition, may be present in association with a metal nanoparticle, or may be released from the composition as vapor depending on the volatility of the anine. In one embodiment, the composition may include an amine present in an amount that is less than 1 weight percent. In one embodiment, the composition may include an amine present in an amount in a range of from 1 weight percent to about 5 weight percent, from about 5 weight percent to about 10 weight percent, from about 10 weight percent to about 25, or from about 25 weight percent to about 50 weight percent. In one embodiment, the composition may include an amine present in an amount in a range that is greater than about 50 weight percent. In one embodiment, the amine produced may be volatile and may be released from the composition during or after the decomposition reaction, and the composition may be free of amine.

In one embodiment, the decomposition reaction may not go to completion, and the composition may include unreacted metal precursor in addition to the decomposition product. In one embodiment, the composition may include unreacted metal precursor and metal nanoparticle. In one embodiment, the composition may include unreacted metal precursor, metal nanoparticle, and an amine. In one embodiment, the composition may include unreacted metal precursor, metal nanoparticle, an amine, and carbon dioxide.

In one embodiment, all the metal in the metal precursor may not be converted to elemental metal (in the metal nanoparticle). In one embodiment, greater than about 90 weight percent of the metal in the metal precursor may be converted to elemental metal. In one embodiment, a weight percent of the metal in the metal precursor that may be converted to elemental metal may be in a range of from about 25 percent to about 40 weight percent, from about 40 weight percent to about 60 weight percent, from about 60 weight percent to about 75 weight percent, or from about 75 weight percent to about 90 weight percent. In one embodiment, less than about 25 weight percent of the metal in the metal precursor may be converted to elemental metal.

As described herein earlier, a nanoparticle may refer to a single particle or may include a plurality of particles (referred to as agglomerates), and the particles having an average particle size on the nano scale. The nanoparticles may be characterized by one or more of average particle size, particle size distribution, average particle surface area, particle shape(s), or particle cross-sectional geometry. A nanoparticle may have a largest dimension (for example, a diameter or length) in the range of from 1 nanometer to 1000 nanometers. In one embodiment, an average particle size of the nanoparticle may be less than 1 nanometer. In one embodiment, an average particle size of the nanoparticle may be in a range of from 1 nanometer to about 10 nanometers, from about 10 nanometers to about 25 nanometers, from about 25 nanometers to about 50 nanometers, from about 50 nanometers to about 75 nanometers, or from about 75 nanometers to about 100 nanometers. In one embodiment, an average particle size of the nanoparticle may be in a range of from about 100 nanometers to about 200 nanometers, from about 200 nanometers to about 300 nanometers, from about 300 nanometers to about 400 nanometers, or from about 400 nanometers to about 500 nanometers.

A plurality of particles may have a distribution of particle sizes that may be characterized by both a number-average size and a weight-average particle size. The number-average particle size may be represented by $S_N = \Sigma(s_i n_i)\Sigma n_i$, where $n_i$ is the number of particles having a particle size $s_i$. The weight average particle size may be represented by $S_W = \Sigma(s_i n_i^2)\Sigma (s_i n_i)$. When all particles have the same size, $S_N$ and $S_W$ may be equal. In one embodiment, there may be a distribution of sizes, and $S_N$ may be different from $S_W$. The ratio of the weight average to the number average may be defined as the polydispersity index ($S_{PDI}$). In one embodiment, $S_{PDI}$ may be equal to about 1. In one embodiment, $S_{PDI}$ may be in a range of from 1 to about 1.2, from about 1.2 to about 1.4, from about 1.4 to about 1.6, or from about 1.6 to about 2.0. In one embodiment, $S_{PDI}$ may be in a range that is greater than about 2.0.

In one embodiment, the metal nanoparticle may include a plurality of particles having a particle size distribution that is a normal distribution, unimodal distribution, a bimodal distribution, or a multi-modal distribution. Certain particle size distributions may be useful to provide certain benefits, and other ranges of particle size distributions may be useful to provide other benefits (for instance, electrical conductivity may require a different particle size range than the other properties). A normal distribution may refer to a distribution of particle sizes with $S_{PDI}$ equal to 1. A unimodal distribution may refer to a distribution of particle sizes having the same particle size. In another embodiment, nanoparticle particles having two distinct size ranges (a bimodal distribution) may be included in the composition: the first range from 1 nanometer to about 10 nanometers, and the second range from about 20 nanometers to about 50 nanometers, for example.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist only of non-spherical particles. For example, such particles may have the form of ellipsoids, which may have all three principal axes of differing lengths, or may be oblate or prelate ellipsoids of revolution. Non-spherical nanoparticles may alternatively be laminar in form, wherein laminar refers to particles in which the maximum dimension along one axis is substantially less than the maximum dimension along each of the other two axes. Such laminar nanoparticles may have a shape similar to the tabular silver halide. Non-spherical nanoparticles may also have the shape of frusta of pyramids or cones, or of elongated rods. In one embodiment, the nanoparticles may be irregular in shape. In one embodiment, the nanoparticle may consist only of spherical particles.

A nanoparticle may have a high surface-to-volume ratio. A nanoparticle may be crystalline or amorphous. In one embodiment, a single type (size, shape, and the like) of nanoparticle may be used, or mixtures of different types of nanoparticles may be used. If a mixture of nanoparticles is used they may be homogeneously or non-homogeneously distributed in the composition.

In one embodiment, the nanoparticles may include one or more active terminations sites on the surfaces (such as hydroxyl groups). In one embodiment, the nanoparticles may be essentially free of active termination sites (such as hydroxyl groups) on the surface. In one embodiment, the nanoparticles may include amine groups on the surface that may passivate the surface of the nanoparticle and reduce any association of particles. In one embodiment, a surface of the nanoparticle may be passivated by amines in-situ, that is, the amines produced in the decomposition reaction may passivate a surface of the metal nanoparticle.

In one embodiment, the nanoparticle may be subjected to a further chemical treatment after the decomposition of the metal precursor. Chemical treatment may include removing polar groups, for example hydroxyl groups, from one or more surfaces of the particles to reduce aggregate and/or agglomerate formation. Chemical treatment may also include functionalizing one or more surfaces of the nanoparticles with functional groups that may improve the compatibility between the nanoparticles and additional materials (for example, a polymer), reduce aggregate and/or agglomerate formation, prevent oxidation of metal nanoparticles, or enhance flow properties of the metal nanoparticles in melt or in solution. In one embodiment, the functional groups may be further reactive and may serve as a platform for the attachment of other chemical species with desirable biological or chemical properties. Suitable functionalizing agents used to functionalize a surface of the metal nanoparticle may include one or more of small organic molecules, polymers, organometallic compounds, or surfactants. Suitable reactive functional groups may include one or more of hydroxyl, thiol, amine, halogen, cyano, sulfhydryl, carboxyl, carbonyl, carbohydrate, vicinal diol, thioether, 2-aminoalcohol, 2-aminothiols, guanidie, imidazole, beta-diketonante or phenol. Suitable passivating functional groups may include one or more of silanes, titanates, or zirconates.

In one embodiment, the metal nanoparticle may be stable towards aggregate formation. An aggregate may include more than one nanoparticle in physical contact with one another. Aggregate should not be confused with agglomerates that are themselves nanoparticles comprising a plurality of nanoscale particles. In some embodiments, the nanoparticles may not be strongly agglomerated and/or aggregated such that the particles may be relatively easily dispersed into a matrix material.

In one embodiment, the metal nanoparticle may include a plurality of particles associated with each other. Associated metal nanoparticles may include aggregates or agglomerates of metal particles. In one embodiment, the metal nanoparticles may be associated each other through formation of bonds or through physical contacts. Association of particles through particle-particle contact may result in an interface between the particle-particle surfaces, which may affect the properties of the composition. Binding of metal-metal nanoparticles may reduce the interfacial surface area.

In one embodiment, two or more metal nanoparticles may bond to each other by one or more of hydrogen bonding, covalent bonding, ionic bonding, or metallurgical bonding. Hydrogen bonding, covalent bonding, or ionic bonding may be effected by functionalizing surfaces of two or more metal nanoparticles with suitable functional groups as described hereinabove. Metallurgical-bonding may be effected by sintering or fusing the metal nanoparticles by application of thermal energy. Metallurgical-bonding, as used herein, may refer to surface diffusion, and/or lattice diffusion, and/or vapor diffusion of metal from one metal particle to another metal particle, which may result in neck formation between two or more metal particles. Neck formation resulting in metallurgical-bonding may provide a continuous conductive connection between two or more metal particles. The diffusion of metal by the aforementioned mechanisms may occur from the surface, and/or grain boundary, and/or bulk of one metal particle to the surface, and/or grain boundary, and/or bulk of another metal particle. Various mechanisms for metallurgical-bonding of the metal particles may be realized. In one example, metallurgical-bonding may occur due to surface diffusion of metal from the surface of one metal particle to the surface/bulk of another metal particle. In another example, metallurgical-bonding may occur due to surface diffusion of metal from the surface of a metal particle into its bulk, followed by bulk diffusion to the surface and neck formation with another particle.

In one embodiment, two or more metal nanoparticles may be metallurgically bonded by heating to a temperature in a range of from about 120 degrees Celsius to about 140 degrees Celsius, from about 140 degrees Celsius to about 160 degrees Celsius, from about 160 degrees Celsius to about 180 degrees Celsius, or from about 180 degrees Celsius to about 200 degrees Celsius. In one embodiment, two or more metal nanoparticles may be metallurgically bonded by heating to a temperature of from about 200 degrees Celsius to about 250 degrees Celsius. In one embodiment, two or more metal nanoparticles may be metallurgically bonded by heating to a temperature lower than a melting temperature of pure metal.

In one embodiment, during decomposition of the metal precursor and prior to metallurgical-bonding, the metal nanoparticle is subjected to a temperature profile having a maximum temperature in a range of less than about 200 degrees Celsius. In one embodiment, during decomposition of the metal precursor and prior to metallurgical-bonding, the metal nanoparticle is subjected to a temperature profile having a maximum temperature in a range of less than about 150 degrees Celsius. In one embodiment, during decomposition of the metal precursor and prior to metallurgical-bonding, the metal nanoparticle is subjected to a temperature profile having a maximum temperature in a range of less than about 120 degrees Celsius. In one embodiment, during decomposition of the metal precursor and prior to metallurgical-bonding, the metal nanoparticle is subjected to a temperature profile having a maximum temperature in a range of less than about 100 degrees Celsius. The temperature profile to which a metal nanoparticle is subjected to may affect the thermal history of the metal nanoparticle. Thermal history may refer to a thermal memory of the metal nanoparticle.

In one embodiment, the composition may include a secondary metal particle. A secondary metal particle as used herein may refer may refer to a single metal particle, a plurality of metal particles, or a plurality of metal particles associated with each other. In one embodiment, the secondary metal particle may include a plurality of particles. The plurality of particles may be characterized by one or more of average particle size, particle size distribution, average particle surface area, particle shape, or particle cross-sectional geometry.

In one embodiment, the secondary metal particle may have an average particle size in the micrometer range or greater than micrometer range, that is, in range of greater than 1 micrometer (or 1000 nanometers). In one embodiment, the secondary metal particle may have an average particle size in a range of from 1 micrometer to about 2 micrometers, from about 2 micrometers to about 4 micrometer, from about 4 micrometers to about 6 micrometers, from about 6 micrometer to about 10 micrometers, from about 10 micrometers to about 25 micrometers, or from about 25 micrometers to about 50 micrometers. In one embodiment, an average particle size of the metal particle may be in a range of from about 50 micrometers to about 100 micrometers, from about 100 micrometers to about 200 micrometer, from about 200 micrometer to about 400 micrometers, from about 400 micrometer to about 600 micrometers, from about 600 micrometers to about 800 micrometers, or from about 800 micrometers to about 1000 micrometers. In one embodiment, an average particle size of the metal particle may be greater than about 1000 micrometers.

A secondary metal particle may include copper, silver, platinum, palladium, gold, tin, indium, aluminum, or a combination of two or more thereof. In one embodiment, the secondary particles and the metal nanoparticle may have substantially the same metallurgy. In one embodiment, the nanoparticle may include a first metal and the secondary particle may include a second metal different than the first metal.

In one embodiment, a metal precursor may be disposed on a surface of the secondary metal particle. The metal precursor may either physically disposed on the surface (for example, coated) or may be bonded to the surface (for example, through hydrogen bonding). During the decomposition of the metal precursor, a metal nanoparticle may be formed and the metal nanoparticle may be associated with the secondary metal particle. As noted herein above, association may be through physical contact or through formation of bonds. In one embodiment, one or more metal nanoparticle may be bonded with one or more secondary metal particle by one or more of hydrogen bonding, covalent bonding, ionic bonding, or metallurgical bonding.

In one embodiment, one or more metal nanoparticles may be bonded with one or more secondary metal particles only through metallurgical bonding. Metallurgical bonding of the metal nanoparticle and secondary metal particle may be realized by heating the composition to a temperature in a range of from about 120 degrees Celsius to about 140 degrees Celsius, from about 140 degrees Celsius to about 160 degrees Celsius, from about 160 degrees Celsius to about 180 degrees Celsius, from about 180 degrees Celsius to about 200 degrees Celsius, or from about 200 degrees Celsius to about 250 degrees Celsius. Various metallurgical bonding configurations of the secondary particle and nanoparticles may be realized or implemented. For example, in certain embodiments, several nanoparticles may be metallurgically-bonded to the same secondary particle. Further, a nanoparticle may metallurgically-bond two secondary particles. In addition, a secondary particle may metallurgically bond to another secondary particle, and so on. In certain configurations, the metallurgical bonding of secondary micron particle to secondary particle may be due, at least in part, to the presence of the nanoparticles.

A composition may include additives. Suitable additives may be selected with reference to performance requirements for particular applications. For example, curing catalyst or initiator may be selected where curing is required, a binder or a matrix (for example a polymer) may be added where certain mechanical properties are desired, a solvent may be added where solution properties may be desired, and the like.

In one embodiment, the composition may include a solvent. A suitable solvent may be aqueous or non-aqueous depending on the solubility of the metal precursor in the particular solvent. Suitable solvents may include aliphatic hydrocarbons, aromatic hydrocarbons, compounds with hydrogen-bond accepting ability, or solvents miscible with water. Suitable aliphatic and aromatic hydrocarbon compounds may include one or more of hexane, cyclohexane, and benzene, which may be substituted with one or more alkyl groups containing from 1-4 carbon atoms. Suitable compounds with hydrogen-bond accepting ability may include one or more of the following functional groups: hydroxyl groups, amino groups, ether groups, carbonyl groups, carboxylic ester groups, carboxylic amide groups, ureido groups, sulfoxide groups, sulfonyl groups, thioether groups, and nitrile groups. Suitable solvents may include one or more alcohols, amines, ethers, ketones, aldehydes, esters, amides, ureas, urethanes, sulfoxides, sulfones, sulfonamides, sulfate esters, thioethers, phosphines, phosphite esters, or phosphate esters. Some other examples of suitable non-aqueous solvents include toluene, hexane, acetone, methyl ethyl ketone, acetophenone, cyclohexanone, 4-hydroxy-4-methyl-2-pentanone, isopropanol, ethylene glycol, propylene glycol, diethylene glycol, benzyl alcohol, furfuryl alcohol, glycerol, cyclohexanol, pyridine, piperidine, morpholine, triethanolamine, triisopropanolamine, dibutylether, 2-methoxyethyl ether, 1,2-diethoxyethane, tetrahydrofuran, p-dioxane, anisole, ethyl acetate, ethylene glycol diacetate, butyl acetate, gamma-butyrolactone, ethyl benzoate, N-methylpyrrolidinone, N,N-dimethylacetamide, 1,1,3,3-tetramethylurea, thiophene, tetrahydrothiophene, dimethylsulfoxide, dimethylsulfone, methanesulfonamide, diethyl sulfate, triethylphosphite, triethylphosphate, 2,2'-thiodiethanol, acetonitrile, or benzonitrile.

In one embodiment, the composition may be free of a solvent. In one embodiment, the composition may include a solvent present in an amount that is in range of less than about 5 weight percent of the composition, in a range of less than about 2 weight percent of the composition, in a range of less than 1 weight percent of the composition, in a range of less than about 0.5 weight percent of the composition, or in a range of less than about 0.1 weight percent of the composition.

In one embodiment, the composition may include a polymer precursor. A polymer precursor may include monomeric species, oligomeric species, mixtures of monomeric species, mixtures of oligomeric species, polymeric species, mixtures of polymeric species, partially-crosslinked species, mixtures of partially-crosslinked crosslinked species, or mixtures of two or more of the foregoing.

A polymer precursor may include reactive groups capable of curing. A reactive group may participate in a chemical reaction when exposed to one or more of thermal energy, electromagnetic radiation, or chemical reagents. Curing may refer to a reaction resulting in polymerization, cross-linking, or both polymerization and cross-linking of the polymer precursor. Cured may refer to a polymer precursor wherein more than about 50 percent of the reactive groups have reacted, or alternatively a percent conversion of the polymer precursor is in a range of greater than about 50 percent. Percent conversation may refer to a percentage of the total number of reacted groups to the total number of reactive groups.

In one embodiment, the composition may include a polymer precursor and a metal precursor. Before, during, or after the decomposition of the metal precursor, the polymer precursor may cure to form a polymeric matrix. A polymeric matrix may include polymeric species, partially-crosslinked species, or crosslinked species.

A polymer precursor may include functional groups that may form cured materials via free radical polymerization, atom transfer, radical polymerization, ring-opening polymerization, ring-opening metathesis polymerization, anionic polymerization, or cationic polymerization. Suitable functional groups may include one or more of alcohol, anhydride, amine, carboxylic acid, acrylate, urethane, urea, melamine, phenol, isocyanate, cyanate ester, epoxy, and the like.

The polymer precursor may include an organic or inorganic backbone depending on the performance requirements of the end-use application of the composition. A suitable organic material may include only carbon-carbon linkages (for example, olefins) or carbon-heteroatom-carbon linkages (for example, ethers, esters and the like) in the main chain. A suitable inorganic backbone for a polymer precursor may include main chain linkages other than that of carbon-carbon linkages or carbon-heteroatom-carbon linkages, for example, silicon-silicon linkages in silanes, silicon-oxygen-silicon linkages in siloxanes, phosphorous-nitrogen-phosphorous linkages in phosphazenes, and the like.

The type of polymer precursor backbone may also affect the dispersion and compatibility properties of the metal precursor. In one embodiment, the polymer precursor may include an organic polymer and the metal precursor may include an organic ligand. The metal precursor may be compatible with the polymer precursor and may be easily dispersible in the organic polymer. In one embodiment, the polymer precursor may include an inorganic polymer and the metal precursor may include an inorganic ligand. The metal precursor may be compatible with the polymer precursor and may be easily dispersible in the inorganic polymer.

The performance properties of the composition may also be affected by the crystallinity and thermal properties of the polymer precursor. A polymer precursor may include or may be capable of forming one or more of an amorphous polymer, a thermoplastic polymer, a crystalline polymer, a thermoset polymer, or combinations of two or more thereof.

A suitable amorphous polymer may include less than that about 5 weight percent of crystalline weight fraction. A suitable amorphous polymer may include less than that bout 2 weight percent of crystalline weight fraction. A suitable amorphous polymer may include less than that 1 weight percent of crystalline weight fraction. A suitable amorphous polymer may include less than that about 0.5 weight percent of crystalline weight fraction. A suitable amorphous polymer may include less than that about 0.1 weight percent of crystalline weight fraction. A suitable crystalline polymer may include greater than that about 5 weight percent of crystalline weight fraction. A suitable crystalline polymer may include greater than that about 10 weight percent of crystalline weight fraction. A suitable crystalline polymer may include greater than that about 25 weight percent of crystalline weight fraction. A suitable crystalline polymer may include greater than that about 50 weight percent of crystalline weight fraction. A suitable crystalline polymer may include greater than that about 75 weight percent of crystalline weight fraction.

A thermoplastic polymer refers to a material with a macromolecular structure that may repeatedly soften when heated and harden when cooled. A thermoset polymer refers to a material which may solidify when first heated under pressure, and which may not be remelted or remolded without destroying its original characteristics. In one embodiment, the polymer precursor may include a thermoplastic polymer and a melting temperature of the thermoplastic polymer may be higher than a decomposition temperature of the metal precursor. In one embodiment, the polymer precursor may include a thermoset polymer and a curing temperature of the thermoset polymer may be the same as a decomposition temperature of the metal precursor. Suitable thermosetting polymeric materials may include one or more epoxides, phenolics, melamines, ureas, polyurethanes, polysiloxanes, or polymers including any suitable crosslinkable functional moieties.

In one embodiment, a polymer precursor consists essentially of an inorganic polymer precursor. In one embodiment, a polymer precursor consists essentially of silicon-oxygen-silicon linkages, such as in siloxanes. Siloxanes may also be referred to as organosiloxanes, where organosiloxanes include silicon-oxygen-silicon linkages and one or more of the silicon atoms is substituted with an organic group. Suitable siloxanes may include linear siloxanes, cyclic siloxanes, branched siloxanes, partially crosslinked siloxanes, or silsesquioxanes. In one embodiment, a siloxane polymer may also be copolymerized with other suitable polymers. Suitable examples of such polymers may include polyimides, polyetherimides, polyamideimides, polyether ether ketones, polyether ketone ketones, polysulfones, polypropylene ethers, polysulfides, or combinations comprising at least one of the foregoing polymers. In one embodiment, the polymer precursor includes elastomeric silicone.

In one embodiment, the polymer precursor consists essentially of a curable material. A polymer precursor may cure in response to a second stimulus. A second stimulus may include thermal energy or electromagnetic radiation. In one embodiment, the first stimulus (for reduction of metal precursor) may be the same as the second stimulus (for curing of polymer precursor). For example, both decomposition reaction of the metal precursor and the curing reaction of the polymer precursor may be initiated by heating the composition. In one embodiment, a curing temperature of the polymer precursor may be in the same range as the decomposition temperature of the metal precursor. In one embodiment, a curing temperature of the polymer precursor may be greater than the decomposition temperature of the metal precursor. In one embodiment, a curing temperature of the polymer precursor may be greater than the decomposition temperature of the metal precursor, and in the same range as that of metallurgical bonding of the metal nanoparticle.

In one embodiment, the curing temperature of the polymer precursor may be in a range of from about room temperature (RT) to about 40 degrees Celsius, from about 40 degrees Celsius to about 60 degrees Celsius, from about 60 degrees Celsius to about 80 degrees Celsius, from about 80 degrees Celsius to about 100 degrees Celsius, from about 100 degrees Celsius to about 120 degrees Celsius, or from about 120 degrees Celsius to about 150 degrees Celsius. In one embodiment, the curing temperature of the polymer precursor may be in a range of from about 150 degrees Celsius to about 175 degrees Celsius, from about 175 degrees Celsius to about 200 degrees Celsius, from about 200 degrees Celsius to about 225 degrees Celsius, or from about 225 degrees Celsius to about 250 degrees Celsius. In one embodiment, the polymer precursor may cure only at a temperature in a range of from about 150 degrees Celsius to about 200 degrees Celsius.

In one embodiment, the polymer precursor consists essentially of a curable siloxane. A curable siloxane may include reactive functionalities such as epoxides, vinyl, vinyl ether, propenylether, epoxides carboxylic, ester, acrylic, alkoxy, or combinations comprising at least one of the foregoing reactive functionalities.

A curable polymer precursor composition may include a catalyst. The catalyst may catalyze (accelerate) a curing reaction of the polymer precursor. The catalyst may catalyze the curing reaction by a free radical mechanism, atom transfer mechanism, ring-opening mechanism, ring-opening metathesis mechanism, anionic mechanism, or cationic mechanism. In one embodiment, a curing catalyst for the polymer precursor (curable polyorganosiloxane) may also function as a reducing agent for the metal precursor, and an additional reducing agent may not be required in the composition. A curing catalyst on activation may reduce a metal cation to its elemental form.

In one embodiment, the polymer precursor consists essentially of a siloxane with one or more cationically curable functional groups. Suitable cationically curable functionalized polyorganosiloxanes may include epoxy-functionalized polyorganosiloxanes, alkenyl ether functionalized polyorganosiloxanes, or a mixture thereof.

In one embodiment, a polyorganosiloxane may include one or more epoxy functional groups. An epoxy-functionalized polyorganosiloxane may be cured by application of thermal energy or electromagnetic radiation. Electromagnetic radiation may include one or more of visible light, ultra-violet radiation, or electron beam radiation. In one embodiment, an epoxy-functionalized polyorganosiloxane may be thermally curable. In one embodiment, an epoxy-functionalized polyorganosiloxane may be curable by ultra-violet radiation.

Suitable epoxy-functionalized polyorganosiloxane may include: .beta.-(3,4-epoxycyclohexyl)ethyltrimethoxy silane, dialkylepoxysiloxy-chain-stopped polydialkyl-alkylepoxysiloxane copolymers, trialkylsiloxy-chain-stopped polydialkyl-alkylepoxysiloxane copolymers, or blends of epoxy functional siloxane copolymers with vinyl and/or propenyl ethers.

In one embodiment, an epoxy-functionalized polyorganosiloxane may include epoxy groups at the chain ends. In one embodiment, an epoxy-functionalized polyorganosiloxane includes dialkylepoxy-chain-stopped polydialkyl alkylepoxysiloxane copolymers. In one embodiment, the polysiloxane units may include lower alkyl substituents, such as methyl groups. The epoxy functionality may be obtained by a hydrosilylation reaction between hydrogen atoms in a polyhydridoalkylsiloxane copolymer and vinyl groups on a vinyl-functional-siloxane cross-linking fluid and other organic molecules, which contain both ethylenic unsaturation and epoxide functionality. Ethylenically unsaturated (allyl or vinyl functionalized) species may add (by a hydrosilylation reaction) to a polyhydridoalkylsiloxane to form a copolymer in the presence of a catalytic amount of precious metal.

A suitable vinyl-functional siloxane cross-linking fluid may include one or more of dimethylvinyl-chain-stopped linear polydimethylsiloxane, dimethylvinyl chain-stopped-polydimethyl-methylvinylsiloxane copolymer, tetravinyltetramethyl cyclotetrasiloxane, or tetramethyldivinyldisiloxane. A suitable polyhydridoalkylsiloxane may include one or more of tetrahydrotetramethylcyclotetrasiloxane, dimethylhydrogen chain-stopped linear polydimethylsiloxane, dimethylhydrogen chain-stopped polydimethyl-methyl-hydrogen siloxane copolymer, or tetramethyldihydrodisiloxane. A suitable vinyl-functional siloxane cross-linking fluid may have a viscosity in a range of from 1 centipoise to about 100,000 centipoise at 25 degrees Celsius. A suitable polyhydridoalkylsiloxane may have a viscosity in a range of from 1 centipoise to about 100,000 centipoise at 25 degrees Celsius.

An ethylenically unsaturated (allyl or vinyl functionalized) species with epoxy groups may include one or more of a cycloaliphatic epoxy compound. Suitable cycloaliphatic epoxy compounds may include one or more of 4-vinylcyclohexeneoxide, allylgycidyl ether or glycidyl acrylate, vinyl-norbornene monoxide, or dicyclopentadiene monoxide. A precious metal catalyst may include one or more of a platinum-metal complex, which may includes complexes of ruthenium, rhodium, palladium, osmium, iridium, or platinum.

An addition or hydrosilylation reaction may be carried out under controlled conditions to prevent complete curing of the siloxane materials. In one embodiment, a "pre-crosslinking" reaction of the siloxane materials may be carried before the final curing reaction. Pre-crosslinking may refer to the ability of the Si—H functional groups in a polyhydridoalkylsiloxane to react with the vinyl groups of a vinyl-functionalized siloxane crosslinking fluid. Pre-crosslinking may provide a composition which may be cured to its final cure state with the expenditure of much less energy than would be needed for a composition that is not so pre-crosslinked. Other siloxane compositions may require large expenditures of energy such as high oven temperatures, in order to cure the product to a final condition. In one embodiment, only small amounts of UV radiation may be necessary to cure the composition in its final state or lower heating temperatures may be required to cure the composition to its final state.

A cationically curable polyorganosiloxane composition may include a cationic initiator. A suitable cationic initiator may include one or more of an onium salt, a Lewis acid, or an alkylation agent. Suitable Lewis acid catalyst may include copper boron acetoacetate, cobalt boron acetoacetate, or both include copper boron acetoacetate and cobalt boron acetoacetate. Suitable alkylation agents may include arylsulfonate esters, for example, methyl-p-toluene sulfonate or methyl trifluoromethanesulfonate. Suitable onium salts may include one or more of an iodonium salt, an oxonium salt, a sulfonium salt, a sulfoxonium salt, a phosphonium salt, a metal boron acetoacetae, a tris(pentafluorophenyl) boron; or arylsulfonate ester. In one embodiment, a suitable cationic initiator may include bisaryliodonium salts, triarylsulphonium salts, or tetraaryl phosphonium salts. A suitable bisaryliodonium salt may include one or more of bis(dodecylphenyl) iodonium hexafluoroantimonate; (octyloxyphenyl, phenyl) iodonium hexafluoro antimonate; or bisaryliodonium tetrakis(pentafluoro phenyl) borate. In one embodiment, the catalyst initiator may include an iodonium salt. In one embodiment, an iodonium salt may also function as a reducing agent and may reduce a metal cation (for example, silver cation) to its elemental form.

In one embodiment, the catalyst may include a free radical initiator that may catalyze a curing reaction of the polyorganosiloxane. A suitable free-radical generating compound may include one or more aromatic pinacols, benzoinalkyl ethers, organic peroxides, and combinations of two or more thereof. In one embodiment, the catalyst may include an onium salt along with a free radical generator. The free radical generating compound may facilitate decomposition of onium salt at a relatively lower temperature.

Other suitable cure catalysts may include one or more of amines, alkyl-substituted imidazole, imidazolium salts, phosphines, metal salts such as aluminum acetyl acetonate (Al (acac)$_3$), or salts of nitrogen-containing compounds with acidic compounds, and combinations thereof. The nitrogen-containing compounds may include, for example, amine compounds, di-aza compounds, tri-aza compounds, polyamine compounds and combinations thereof. The acidic compounds may include phenol, organo-substituted phenols, carboxylic acids, sulfonic acids and combinations thereof. A suitable catalyst may be a salt of nitrogen-containing compounds. Salts of nitrogen-containing compounds may include, for example 1,8-diazabicyclo(5,4,0)-7-undecane. A suitable catalyst may include one or more of triphenyl phosphine (TPP), N-methylimidazole (NMI), and dibutyl tin dilaurate (DiBSn). The catalyst may be present in an amount in a range of from about 10 parts per million (ppm) to about 10 weight percent of the total composition.

Suitable curable epoxy-functionalized polyorganosiloxanes may be commercially available from GE Silicones under the trade names of UV9300, UV9315, UV9400, UV500A, UV9320, or UV9500. The polyorganosiloxanes may include dimethylepoxysilyloxy-stopped linear polydimethyl-methylepoxysiloxane, where the epoxy group is a 3,4-epoxy-2-ethyl-cyclohexyl group.

In one embodiment, the polymer precursor consists essentially of a siloxane curable by a hydrosilylation reaction. A polymer precursor may include a polysiloxane having an average of at least two silicon-bonded alkenyl groups per molecule and a hydridopolysiloxane having at least two silicon-bonded hydrogen atoms.

An alkenyl functionalized polysiloxane may include structural units of formula:

$$M'_e D'_f D''_g T'_h Q'_i \qquad (IX)$$

wherein M' has formula:

$$R^{13}R^{14}R^{15}SiO_{1/2}; \qquad (X)$$

D' has the formula:

$$R^{16}R^{17}SiO_{2/2}; \qquad (XI)$$

D'' has the formula $$R^{18}R^{19}SiO_{2/2}; \qquad (XII)$$

T' has the formula $$R^{20}SiO_{3/2}; \text{ and} \qquad (XIII)$$

Q' has the formula $$SiO_{4/2} \qquad (XIV)$$

wherein $R^{13}$, $R^{14}$, $R^{16}$, $R^{17}$, $R^{18}$ and $R^{20}$ are independently in each instance an aliphatic radical, a cycloaliphatic radical, or an aromatic radical, and $R^{15}$ and $R^{19}$ are independently at each instance an alkenyl radical. The stoichiometric coefficients "e" and "f" are non-zero and positive while the stoichiometric coefficients "g", "h" and "i" are zero or positive subject to the requirement that "a"+"c" is greater than or equal to 2. The stoichiometric coefficients "b" and "c" may be chosen such that the viscosity of the alkenyl bearing polysiloxane ranges from about 50 to about 200,000 centistokes at 25 degrees Celsius, from about 100 to about 100,000 centistokes at 25 degrees Celsius, from about 200 to about 50,000 centistokes at degrees Celsius, and from about 275 to about 30,000 centistokes at degrees Celsius.

A hydridopolysiloxane may include structural units of formula $$M''_j D^{iv}_k D^v_l T''_m Q''_n \quad (XV)$$

wherein M" has formula:

$$R^{21}R^{22}R^{23}SiO_{1/2}; \quad (XVI)$$

$D^{iv}$ has the formula:

$$R^{24}R^{25}SiO_{2/2}; \quad (XVII)$$

$D^v$ has the formula $$R^{26}R^{27}SiO_{2/2}; \quad (XVIII)$$

T" has the formula $$R^{28}SiO_{3/2}; \text{ and} \quad (XIX)$$

Q" has the formula $$SiO_{4/2} \quad (XX)$$

wherein $R^{21}$, $R^{22}$, $R^{24}$, $R^{25}$, $R^{26}$ and $R^{28}$ are independently in each instance an aliphatic radical, a cycloaliphatic radical, or an aromatic radical, and $R^{15}$ and $R^{19}$ are independently at each instance a hydrogen. The stoichiometric coefficients "j" and "l" are non-zero and positive while the stoichiometric coefficients "k", "m" and "n" are zero or positive subject to the requirement that "j"+"l" is greater than or equal to 2. The stoichiometric coefficients "j" and "l" may be chosen such that the viscosity of the hydrogen bearing hydridopolysiloxane ranges from 1 to about 200,000 centistokes at 25 degrees Celsius, from about 5 to about 10,000 centistokes at degrees Celsius, from about 10 to about 5000 centistokes at 25 degrees Celsius, and from about 25 to about 500 centistokes at 25 degrees Celsius.

Alkenyl groups bonded with silicon atoms may include vinyl groups, allyl groups, butenyl groups, pentenyl groups, hexenyl groups, or heptenyl groups. Alkene groups may be attached at backbone ends or as side chains to the backbone. Organic groups that may be bonded with the silicon atoms in addition to the alkenyl groups may include alkyl groups such as methyl groups, ethyl groups, propyl groups, butyl groups, pentyl groups, hexyl groups, or heptyl groups; aryl groups such as phenyl groups, tolyl groups, xylyl groups, or naphthyl groups; aralkyl groups such as benzyl groups or phenethyl groups; or halogenated groups such as chloromethyl groups, 3-chloropropyl groups, or 3,3,3-trifluoropropyl groups. Molecular structure of the organopolysiloxane may be straight chain form, a straight chain form having some branches, a cyclic form, or a branched chain form.

An alkenyl-substituted organopolysiloxane may include copolymers of dimethyl siloxane blocked with trimethylsiloxy groups at both terminals of the molecular chain and of methyl vinyl siloxane; methyl vinyl polysiloxane blocked with trimethylsiloxy groups at both terminals of the molecular chain; copolymers of dimethyl siloxane blocked with trimethylsiloxy groups at both terminals of the molecular chain, methyl vinyl siloxane, methyl phenyl siloxane; dimethyl polysiloxane blocked with dimethylvinyl siloxane groups at both terminals of the molecular chain; methyl vinyl polysiloxane blocked with dimethyl vinyl siloxane groups at both terminals of the molecular chain; copolymers of dimethyl siloxane blocked with dimethyl vinyl siloxane groups at both terminals of the molecular chain and of methyl vinyl siloxane; or copolymers of dimethyl siloxane blocked with dimethyl vinyl siloxane groups at both terminals of the molecular chain.

Hydrogen atoms may be attached at backbone ends or as side chains to the backbone. Organic groups bonded with silicon atoms of the organohydridopolysiloxane may include alkyl groups such as methyl groups, ethyl groups, propyl groups, butyl groups, pentyl groups, hexyl groups, or heptyl groups; aryl groups such as phenyl groups, tolyl groups, xylyl groups, or naphthyl groups; aralkyl groups such as phenethyl groups; or halogenated alkyl groups such as chloromethyl groups, 3-chloropropyl groups, or 3,3,3-trifluoropropyl groups.

An organohydridopolysiloxane may include methylhydrogen polysiloxane blocked with trimethylsiloxy groups at both terminals of the molecular chain, copolymers of dimethyl siloxane blocked with trimethylsiloxy groups at both terminals of the molecular chain and of methylhydrogen siloxane; copolymers of dimethyl siloxane blocked with trimethylsiloxy groups at both terminals of the molecular chain, methylhydrogen siloxane and methylphenyl siloxane; dimethyl polysiloxane blocked with dimethylhydrogen siloxane groups at both terminals of the molecular chain; dimethyl polysiloxane blocked with dimethylhydrogen siloxane groups at both terminals of the molecular chain; copolymers of dimethyl blocked with dimethylhydrogen siloxane groups at both terminals of the molecular chain; or methylphenyl polysiloxane blocked with dimethylhydrogen siloxane groups at both terminals of the molecular chain.

Hydrosilylation reaction may be catalyzed by use of hydrosilylation catalysts. Suitable hydrosilylation catalysts may include one or more of rhodium, platinum, palladium, nickel, rhenium, ruthenium, osmium, copper, cobalt or iron. Suitable platinum catalysts may be used for the hydrosilylation reaction. A suitable platinum compound may have the formula $(PtCl_2Olefin)$ or $H(PtCl_3Olefin)$. Another suitable platinum catalyst may include a cyclopropane complex or a complex formed from chloroplatinic acid with up to 2 moles per gram of platinum and one or more of alcohols, ethers, or aldehydes.

In one embodiment, a hydrosilylation catalyst for the polymer precursor (curable polyorganosiloxane) may also function as a reducing agent for the metal precursor, and an additional reducing agent may not be required in the composition. A hydrosilylation catalyst on activation may reduce a metal cation to its elemental form. In one embodiment, a hydridopolysiloxane may function as a reducing agent for the metal precursor.

A hydrosilylation catalyst inhibitor may be included in the composition. A hydrosilylation catalyst inhibitor may modify the curing profile to achieve the desired shelf life. Addition of hydrosilylation catalyst inhibitors may also delay the onset of curing and hence allow sufficient time for decomposition of the metal precursor. Curing of polysiloxanes before decomposition may result in increase in viscosity and hence an intractable composition. Suitable hydrosilylation catalyst inhibitors may include maleates, alkynes, phosphites, alkynols, fumarates, succinates, cyanurates, isocyanurates, alkynylsilanes, vinyl-containing siloxanes, or combinations thereof. Suitable hydrosilylation catalyst inhibitors may include esters of maleic acid (e.g. diallylmaleate, dimethylmaleate), acetylenic alcohols (e.g., 3,5 dimethyl-1-hexyn-3-ol and 2 methyl-3-butyn-2-ol), amines, tetravinyltetramethylcyclotetrasiloxane, or mixtures of two or more thereof.

Average molecular weight of the polymer precursor may depend upon one or more of the desired end-use properties of the composition, the conditions to be used during processing of the composition, or degree of compatibility between the different components of the composition. In one embodiment, a polymer precursor may have a number average molecular weight in a range of from about 50 grams per mole to about 100 grams per mole, from about 100 grams per mole to about 200 grams per mole, from about 200 grams per mole to about 500 grams per mole, from about 500 grams per mole to about 1000 grams per mole, from about 1000 grams per mole to about 2500 grams per mole, from about 2500 grams per mole to about 5000 grams per mole, from about 5000 grams per mole to about 10000 grams per mole, from about 10000 grams per mole to about 25000 grams per mole, from about 25000 grams per mole to about 50000 grams per mole, or from about 50000 grams per mole to about 100000 grams per mole. In one embodiment, a polymer precursor may have a number average molecular weight of greater than about 100000 grams per mole.

In one embodiment, a number average molecular weight of the polymer matrix may be greater than about 10000 grams/mole. In one embodiment, the number average molecular weight of the polymer matrix may be in a range from about 10000 grams/mole to about 50000 grams/mole, from about 50000 grams/mole to about 100000 grams/mole, from about 100000 grams/mole to about 250000 grams/mole, from about 250000 grams/mole to about 500000 grams/mole, or from about 500000 grams/mole to about 1000000 grams/mole. In one embodiment, the number average molecular weight of the polymer matrix may be greater than about $10^6$ grams/mole.

Suitable amine hardeners may include aromatic amines, aliphatic amines, or combinations thereof. Aromatic amines may include, for example, m-phenylene diamine, 4,4'-methylenedianiline, diaminodiphenylsulfone, diaminodiphenyl ether, toluene diamine, dianisidene, and blends of amines. Aliphatic amines may include, for example, ethyleneamines, cyclohexyldiamines, alkyl substituted diamines, methane diamine, isophorone diamine, and hydrogenated versions of the aromatic diamines. Combinations of amine hardeners may be used.

Suitable phenolic hardeners may include phenol-formaldehyde condensation products, commonly named novolac or cresol resins. These resins may be condensation products of different phenols with various molar ratios of formaldehyde. Such novolac resin hardeners may include those commercially available such as TAMANOL 758 or HRJ1583 oligomeric resins available from Arakawa Chemical Industries and Schenectady International, respectively.

Suitable hydroxy aromatic compounds may include one or more of hydroquinone, resorcinol, catechol, methyl hydroquinone, methyl resorcinol and methyl catechol. Suitable anhydride hardeners may include one or more of methyl hexahydrophthalic anhydride; methyl tetrahydrophthalic anhydride; 1,2-cyclohexanedicarboxylic anhydride; bicyclo (2.2.1) hept-5-ene-2,3-dicarboxylic anhydride; methyl bicyclo (2.2.1) hept-5-ene-2,3-dicarboxylic anhydride; phthalic anhydride; pyromellitic dianhydride; hexahydrophthalic anhydride; dodecenylsuccinic anhydride; dichloromaleic anhydride; chlorendic anhydride; tetrachlorophthalic anhydride; and the like. Combinations comprising at least two anhydride hardeners may be used. Anhydrides may hydrolyze to carboxylic acids useful for fluxing. In certain embodiments, a bifunctional siloxane anhydride may be used as a hardener, alone or in combination with at least one other hardener. Additionally, cure catalysts or organic compounds containing hydroxyl moiety may be added with the anhydride hardener.

In one embodiment, a reactive organic diluent may be added to the composition. A reactive organic diluent may include monofunctional compounds (having one reactive functional group) and may be added to decrease the viscosity of the composition. Suitable examples of reactive diluents may include 3-ethyl-3-hydroxymethyl oxetane; dodecylglycidyl; 4-vinyl-1-cyclohexane diepoxide; di (beta-(3,4-epoxycyclohexyl)ethyl) tetramethyldisiloxane; and the like. Reactive organic diluents may include monofunctional epoxies and/or compounds containing at least one epoxy functionality. Representative examples of such diluents may include alkyl derivatives of phenol glycidyl ethers such as 3-(2-nonylphenyloxy)-1,2-epoxypropane or 3-(4-nonylphenyloxy)-1,2-epoxypropane. Other diluents which may be used may include glycidyl ethers of phenol itself and substituted phenols such as 2-methylphenol, 4-methyl phenol, 3-methylphenol, 2-butylphenol, 4-butylphenol, 3-octylphenol, 4-octylphenol, 4-t-butylphenol, 4-phenylphenol and 4-(phenyl isopropylidene) phenol. An unreactive diluent may also be added to the composition to decrease the viscosity of the formulation. Examples of unreactive diluents include toluene, ethylacetate, butyl acetate, 1-methoxy propyl acetate, ethylene glycol, dimethyl ether, and combinations thereof.

In one embodiment, an adhesion promoter may be included in the composition. Suitable adhesion promoters may include one or more of trialkoxyorganosilanes (for example, γ-aminopropyltrimethoxysilane, 3-glycidoxy propyltrimethoxysilane, and bis(trimethoxysilylpropyl)fumarate). If present, the adhesion promoters may be added in an effective amount. An effective amount may be in a range of from about 0.01 weight percent to about 2 weight percent of the total final composition.

In one embodiment, flame retardants may be included in the composition. Suitable examples of flame retardants may include or more of phosphoramides, triphenyl phosphate ("TPP"), resorcinol diphosphate ("RDP"), bisphenol-a-disphosphate ("BPA-DP"), organic phosphine oxides, halogenated epoxy resin (tetrabromobisphenol A), metal oxide, metal hydroxides, and combinations thereof. When present, the flame retardant may be in a range of from about 0.5 weight percent to about 20 weight percent relative to the total weight. Defoaming agents, dyes, pigments, binders (other than the polymer precursor), and the like may also be incorporated into composition. The amount of such additives may be determined by the end-use application.

In one embodiment, the composition may include a filler in addition to the metal nanoparticle and the secondary metal particle. A filler may be included to control one or more electrical property, thermal property, or mechanical property of the filled composition. In one embodiment, the metal nanoparticle, secondary metal particle, or filler selection may be based on the desired electrical properties, thermal properties or both electrical and thermal properties of a feature (for example, a layer) formed from the composition.

In one embodiment, a filler may include electrically conducting particles. Suitable electrically conducting particles may include one or more of metals, semi-conducting materials, carbonaceous materials (such as carbon black or carbon nanotubes), or electrically conductive polymers.

In one embodiment, a filler may include a plurality of thermally conducting particles. Suitable thermally conducting particles may include one or more of siliceous materials (such as fumed silica, fused silica, or colloidal silica), carbonaceous materials, metal hydrates, metal oxides, metal borides, or metal nitrides.

In one embodiment, a filler may include silica and the silica may be colloidal silica. Colloidal silica may be a dispersion of submicron-sized silica ($SiO_2$) particles in an aqueous or other solvent medium. The total content of silicon dioxide in the composition may be in the range from about 0.001 to 1 weight percent, from 1 weight percent to about 10 weight percent, from about 10 weight percent to about 20 weight percent, from about 20 weight percent to about 50 weight percent, or from about 50 weight percent to about 90 weight percent of the total composition weight.

In one embodiment, colloidal silica may include compatibilized and passivated colloidal silica. Compatibilized and passivated silica may serve to reduce a coefficient of thermal expansion (CTE) of the composition, may function as spacers to control bond-line thickness, or both. In one embodiment, a plurality of particles (that is, silica filler) may be compatibilized and passivated by treatment with at least one organoalkoxysilane and at least one organosilazane. The two-component treatment may be done sequentially or may be done simultaneously. Filled compositions that include compatibilized and passivated particles may show relatively better room temperature stability than analogous formulations in which colloidal silica has not been passivated. In some cases, increasing room temperature stability of the resin formulation may allow for higher loadings of curing agents, hardeners, and catalysts that might otherwise be undesirable due to shelf life constraints. By increasing those loadings, a higher degree of cure, a lower cure temperature, or more sharply defined cure temperature profiles may be achievable. In one embodiment, the filler having colloidal and functionalized silica may include micrometer-size fused silica. When present, the fused silica fillers may be added in an effective amount to provide thermal conductivity, as spacers to control bond-line thickness, and the like.

In one embodiment, the metal nanoparticle may be present in an effective amount. An effective amount of metal nanoparticle refers to amount of elemental metal sufficient to meet the performance requirements of the end-use application. In one embodiment, the composition may have metal nanoparticle present in an amount sufficient to have has one or more of a desired biocidal property, electrical property, thermal property, optical property, or catalytic property.

In one embodiment, the metal nanoparticle may be present in an amount that is sufficient to render the composition electrically conductive, thermally conductive, or both electrically and thermally conductive. In one embodiment, the metal nanoparticle may be present in an amount that is sufficient to bond with one or more metal nanoparticle, with one or more secondary particle, or with both a metal nanoparticle and a secondary particle. In one embodiment, the metal nanoparticle is present in an amount such that, after sintering or metallurgically bonding the metal nanoparticles and secondary particles (if present), there is a continuous electrical communication or conductive pathway from one of the particles to another. In one embodiment, the metal nanoparticle may be present in an amount such that in addition to the conductive properties, the composition may meet other performance requirements. Examples of other performance requirements may include Theological properties of the composition, processability of the composition, stability of the composition, and the like.

In one embodiment, the composition may include a metal nanoparticle present in an amount that is less than about 0.1 weight percent. In one embodiment, the composition may include a metal nanoparticle present in an amount in a range of from about 0.1 weight percent to 1 weight percent, from 1 weight percent to about 2 weight percent, from about 2 weight percent to about 5 weight percent, from about 5 weight percent to about 10 weight percent of the composition. In one embodiment, the composition may include a metal nanoparticle present in an amount in a range of from about 10 weight percent to about 20 weight percent, from about 20 weight percent to about 30 weight percent, from about 30 weight percent to about 40 weight percent, or from about 40 weight percent to about 50 weight percent of the composition. In one embodiment, the composition may include a metal nanoparticle present in an amount that is greater than about 40 weight percent.

In one embodiment, the composition may have a viscosity (solution or melt) or a surface tension so as to be printable on a surface of a substrate. A substrate may include paper, ceramic, metal, glass, or a polymeric material. Printable may refer to flow properties of the composition such that the composition may be disposed on the surface of the substrate in predetermined patterns. After the formation of pattern, the composition may have be semi-rigid or in the form of a paste, such that the integrity of the patterns may be maintained. In certain embodiments, the composition may be cured to obtain permanent patterns.

In one embodiment, the composition may have a viscosity (solution or melt) or a surface tension so as to be printable on a surface of a substrate by one or more of stencil printing, screen-printing, intaglio printing, gravure printing, lithographic printing, and flexographic printing. In one embodiment, the composition may have a viscosity (solution or melt) or a surface tension so as to be printable on a surface of a substrate by a direct write method such as ink-jet printing, an aerosol jet, or using an automated syringe.

In one embodiment, the composition may have a surface tension in a range of from about 5 dynes/centimeters to about 10 dynes/centimeters, from about 10 dynes/centimeters to about 20 dynes/centimeters, from about 20 dynes/centimeters to about 30 dynes/centimeters, from about 30 dynes/centimeters to about 40 dynes/centimeters, or from about from about 40 dynes/centimeters to about 50 dynes/centimeters.

In one embodiment, the composition may have a solution viscosity or a melt viscosity in a range of from about 10 centipoise to about 50 centipoise, from about 50 centipoise to about 100 centipoise, from about 100 centipoise to about 250 centipoise, from about 250 centipoise to about 500 centipoise, or from about 500 centipoise to about 1000 centipoise. In one embodiment, the composition may have a solution or melt viscosity in a range of from about 1000 centipoise to about 2000 centipoise, from about 2000 centipoise to about 3000 centipoise, from about 3000 centipoise to about 4000 centipoise, or from about 4000 centipoise to about 5000. For use in an ink-jet device, a viscosity of the composition may be less than about 50 centipoise. For use in aerosol jet atomization, a viscosity of the composition may be in a range that is less than about 20 centipoise. Automated syringes may use compositions having a higher viscosity, that is, greater than about 5000 centipoise.

Stability of the composition may depend on one or more of particle concentration, temperature, ambient conditions, and the like. In one embodiment, the composition may be stable at a temperature in a range of greater than about 20 degrees Celsius for a period of greater than 1 day. In one embodiment, the composition may be stable at a temperature in a range of from about 20 degrees Celsius to about 50 degrees Celsius, from about 50 degrees Celsius to about 75 degrees Celsius, from about 75 degrees Celsius to about 100 degrees Celsius, from about 100 degrees Celsius to about 150 degrees Celsius, or from about 150 degrees Celsius to about 175 degrees Celsius, and for a period of greater than 1 day. In one embodiment, the composition may be stable at a temperature in a range of greater than about 175 degrees Celsius for a period of greater than 1 day. In one embodiment, the composition may be stable at a temperature in a range of greater than about 175 degrees Celsius for a period of greater than about 10 days. In one embodiment, the composition may be stable at a temperature in a range of greater than about 175 degrees Celsius for a period of greater than about 30 days. In one embodiment, a composition may be stored without refrigeration for a period of greater than 1 day.

In one embodiment, the composition may be patterned on a surface of a substrate in the form of one or more conductive features. Conductive feature may refer to a pattern on a surface of the substrate that may be electrically conductive. The features may have a minimum feature size that is in a range of less than about 200 micrometers, in a range of less than about 100 micrometers, in a range of less than about 75 micrometers, in a range of less than about 50 micrometers, or in a range of less than about 25 micrometers. In some embodiments, the minimum feature size may be in a range of less than about 10 micrometers. The minimum feature size may be the size of the smallest dimension of a feature in the x-y plane, such as the width of a conductive trace.

A conductive feature may have a wide range of electrical characteristics depending on the type of electrical feature desired and the materials in the composition. In one embodiment, the conductive feature may have an electrical resistivity in a range of less than about $10^{-6}$ Ohm centimeter, less than about $10^{-5}$ Ohm centimeter, less than about $10^{-4}$ Ohm centimeter, or less than about $10^{-3}$ Ohm centimeter.

Compositions and conductive features according to an embodiment of the invention may be used in a flat display panel, an organic light emitting diode, a thin film transistor, a liquid crystal display, a radio frequency identification tag, sensors, novelty electronics (for example games, greeting cards), and the like. In one embodiment, the compositions may be used to form active and passive electrical patterns in flexible electronics.

In one embodiment, the composition includes a curable polymer precursor and a metal precursor. In one embodiment, the composition is free of solvent and organic diluent is included in the composition to improve the dispersion and rheological properties of the composition.

A solvent-free composition in accordance with one embodiment, of the invention may have sufficiently low viscosity such that the composition may flow into a space, for example, defined by opposing surfaces of a chip and a substrate. In one embodiment, a composition may have a room temperature viscosity in a range of less than about 20000 centipoise. In one embodiment, a composition may have a room temperature viscosity in a range of from about 100 centipoise to about 1000 centipoise, from about 1000 centipoise to about 2000 centipoise, from about 2000 centipoise to about 5000 centipoise, from about 5000 centipoise to about 10000 centipoise, from about 10000 centipoise to about 15000 centipoise, or from about 15000 centipoise to about 20000 centipoise.

In one embodiment, the composition (prior to or after curing) may be free of solvent of other volatiles. Volatiles may result in formation of voids during one or more processing steps, for example, during decomposition of the metal precursor. Voids may result in undesirable defect formation. In one embodiment, the composition produces an insufficient amount of gas to form visually detectable voids prior to, during, or after curing.

In one embodiment, the polymer precursor is cured to form a cured composition. The polymer precursor may be cured during or after the decomposition of the metal precursor. A cured composition may be characterized by one or more properties such as mechanical properties, electrical properties, Theological properties, and the like. Performance properties may depend on one or more of the metal precursor amount, size, shape, and amount of metal nanoparticles, the type and concentration of polymer precursor, and the like.

In one embodiment, the cured composition may be electrically conductive. In one embodiment, a cured composition may have an electrical resistivity that is in a range of less about $10^{-3}$ Ohm centimeter, in a range of less than about $10^{-4}$ Ohm centimeter, in a range of less than about $10^{-5}$ Ohm centimeter, or in a range of less than about $10^{-6}$ Ohm centimeter. In one embodiment, the cured composition may have electrical properties that may not vary significantly over a period of time. In one embodiment, the cured composition may have an electrical resistivity values such that the electrical resistivity decreases by an amount that is less than about 30 percent, at room temperature after a duration of about 1000 hours. In one embodiment, the cured composition may have an electrical resistivity values such that the electrical resistivity decreases by an amount that is less than about 20 percent, at room temperature after a duration of about 1000 hours. In one embodiment, the cured composition may have an electrical resistivity values such that the electrical resistivity decreases by an amount that is less than about 10 percent, at room temperature after a duration of about 1000 hours.

In one embodiment, a composition may have an electrical resistance in a range of from about 0.001 ohms to about 0.005 ohms, from about 0.005 ohms to about 0.01 ohms, from about 0.01 ohms to about 0.025 ohms, from about 0.025 ohms to about 0.05 ohms, from about 05 ohms to about 0.1 ohms, from about 0.1 ohms to about 0.5 ohms, from about 0.5 ohms to 1 ohms, or from 1 ohms to about 2 ohms.

In addition to the being electrically conductive, a cured composition may also be thermally conductive. In one embodiment, a cured composition may have a thermal conductivity in a range of greater than 1 W/mK at 100 degrees Celsius, greater than about 2 W/mK at 100 degrees Celsius, greater than about 5 W/mK at 100 degrees Celsius, greater than about 10 W/mK at 100 degrees Celsius, or greater than about 20 W/mK at 100 degrees Celsius.

In one embodiment, the cured composition may have a thermal resistance in a range of from about 0.1 mm$^2$ K/W to about 0.5 mm$^2$K/W, from about 0.5 mm$^2$ K/W to about 2 mm$^2$K/W, from about 2 mm$^2$K/W to about 10 mm$^2$K/W, from about 10 mm$^2$K/W to about 25 mm$^2$ K/W, from about 25 mm$^2$ K/W to 50 mm$^2$ K/W, from about 50 mm$^2$K/W to about 100 mm$^2$K/W, from about 100 mm$^2$K/W to about 150 mm 2 K/W, or from about 150 mm$^2$K/W to about 200 mm$^2$K/W.

Mechanical properties (such as modulus) and thermal properties of the cured composition may also depend on the glass temperature of the composition. In one embodiment, a glass transition temperature of the cured composition may be greater than about 150 degrees Celsius, greater than about 200 degrees Celsius, greater than about 250 degrees Celsius, greater than about 300 degrees Celsius, or greater than about 350 degrees Celsius. In one embodiment, a modulus of the cured composition may be in a range of greater than about 2000 MegaPascals, greater than about 3000 MegaPascals, greater than about 5000 MegaPascals, greater than about 7000 MegaPascals, or greater than about 10000 MegaPascals.

In one embodiment, a conductive adhesive may include a composition as described hereinabove. A conductive adhesive may include a polymer precursor and a metal precursor. In one embodiment a conductive adhesive may be cured to form a cured adhesive composition. A cured conductive adhesive may include a cured product of the polymer precursor (polymeric matrix), one or more metal nanoparticles, and one or more secondary metal particles (if present).

A conductive adhesive (cured or not) may function to adhere or attach a surface of a substrate to a surface of a circuit device. Effectiveness of the cured composition in adhering a circuit device to the substrate may depend on factors such as interfacial adhesion between the cured composition and the chip or the substrate or shrinkage (if any) after curing of the composition. Interfacial properties between the cured composition and the chip or the substrate may be improved by choosing a curable polymer precursor with the desired interfacial properties, for example adhesive properties. In one embodiment, the adhesive composition may form a continuous interfacial contact with a substrate prior to curing. In one embodiment, the adhesive composition may form a continuous interfacial contact with a chip prior to curing. In one embodiment, the cured adhesive composition may form a continuous interfacial contact with a substrate and a chip after curing.

In one embodiment, the cured composition may have a die shear adhesion strength in a range of form about 50 pounds per square inch (psi) to about 75 psi, from about 75 psi to about 100 psi, from about 100 psi to about 200 psi, from about 200 psi to about 400 psi, from about 400 psi to about 600 psi, from about 600 psi to about 800 psi, or from about 800 psi to about 1000 psi.

In addition to functioning as an adhesive, a conductive adhesive may also function to provide a continuous electrical or thermal contact between the substrate (for example, a heat sink) and the circuit device (for example, a chip). In one embodiment, a continuous electrical or thermal connect may be obtained by metallurgically bonding a plurality of metal nanoparticles and a plurality of secondary metal particles. Various metallurgical bonding configurations of the secondary particles and nanoparticles may be realized or implemented. For example, in certain embodiments, several nanoparticles may be metallurgically bonded to the same secondary particle. In certain embodiment, a nanoparticle may metallurgically couple two micrometer-sized particles to each other, and which in turn may be individually bonded to one or more metal nanoparticles. A nanoparticle or a secondary metal particle may also be in contact with a circuit device, a substrate, or both circuit-device and substrate. The different metallurgical bonding configurations between the metal nanoparticles and the secondary metal particles may result in a continuous conductive pathway between the circuit-device and the substrate.

A conductive adhesive, according to an embodiment of the invention, may be used in the fabrication of electronic devices, integrated circuits, semiconductor devices, and the like. A conductive adhesive composition described herein, may find use as lead-free solder replacement technology, general interconnect technology, die attach adhesive, as an isotropic conductive adhesive (ICAs), as a thermal interface material (TIM), an electromagnetic interference/radio frequency interference shielding composite, and the like. Suitability of the conductive adhesive for a particular application may depend on one or more of the electrical, thermal, mechanical, or flow properties of the composition. Thus, by way of example, an electrical connect may require an electrically conductive composition, while a thermal interface material may require a composition that is thermally conductive and is electrically insulating (in certain instances).

In one embodiment, an article may include a circuit-device; a substrate and a conductive adhesive composition disposed between the circuit-device and the substrate. A conductive adhesive composition may be cured on uncured.

In one embodiment, a conductive adhesive composition, as described herein, may be capable of providing a continuous thermal pathway between the circuit device and substrate. The conductive adhesive may be used a thermal interface material. As a thermal interface material, the conductive adhesive may facilitate heat transfer from the chip to the substrate. The substrate in turn may be coupled to a heat-dissipating unit, such a heat sink, heat radiator, or a heat spreader. Device miniaturization in electronic application may necessitate devices with fine pitch capabilities. Nano-sized particles may facilitate fabrications of devices with fine pitch capabilities. In one embodiment, nano-sized particles may provide bond-line thickness in a thermal interface material that may be smaller that a bond-line thickness achievable using micron-sized particles. In one embodiment, metallurgical-bonding of nanoparticles to secondary particles may provide compositions with the desired performance characteristics for a thermal interface material using lower amounts of nanoparticles and secondary particles in the adhesive composition.

In one embodiment, a conductive adhesive, as described herein, may be capable of providing a continuous electrical pathway between the circuit-device and the substrate. A conductive adhesive may be used as an electrical interconnect. A suitable circuit-device may include a chip. In one embodiment, a conductive adhesive as described herein may be used as a lead-free conductive adhesive. A lead-free conductive adhesive may be free of lead. In one embodiment, a lead-free conductive adhesive may include lead present in an amount in a range that is less than about 0.1 weight percent, in a range that is less than about 0.5 weight percent, or in a range that is less than 1 weight percent of the composition. A lead-free conductive adhesive may replace a lead-based solder used to connect a chip to a substrate. In one embodiment, a lead-free conductive adhesive, as described herein may provide electrical properties (resistivity or resistance) on the order of a lead-based solder, such as a eutectic lead-tin solder. In one embodiment, a lead-free conductive adhesive may electrically connect a circuit device to a non-solderable substrate or a thermally sensitive substrate (for example, glass, plastic, and the like).

In one embodiment, a method of making a carbamate-containing metal precursor is provided. In one embodiment, the method may include contacting an amine with a carbon dioxide source under suitable reaction conditions. Reaction of an amine with carbon dioxide may result in formation of a carbamic acid. A carbamic acid may be further reacted with a metal cation to form a metal carbamate. In one embodiment, the method may include contacting an amine, a carbon dioxide source, and a metal cation simultaneously to form the metal carbamate. A metal carbamate may function as a metal precursor in one embodiment.

A carbon-dioxide source may include carbon dioxide gas or other compounds, such as carbonates, and the like. A metal cation may include one or more metal oxide or metal salt. In one embodiment silver oxide may be used.

An amine may include an organic backbone or an inorganic backbone. Choice of a suitable amine may depend upon the ligand properties desired. Stability of the metal precursor may depend on the type and molecular weight of the ligand. In one embodiment, an amine may be chosen such that the metal precursor may be stable at room temperature and may decompose at the required decomposition temperature. Choice of the amine may also affect the compatibility of the metal precursor with the polymer precursor (if used). For example, inorganic amines may facilitate dispersion of metal precursors in inorganic polymer precursors. Similarly, surface characteristics of the metal nanoparticle may be affected by the nature of the amine. In one embodiment, after the decomposition of the metal precursor, an inorganic amine may be disposed on the surface of the metal nanoparticle and facilitate dispersion of the metal nanoparticle in the polymer precursor.

In one embodiment, an amine may include an organic backbone. In one embodiment, an aliphatic amine may be used. Length of the alkyl chain may determine the stability of the amine and the corresponding carbamate at room temperature. Length of the alkyl chain may also determine the decomposition temperature of the corresponding carbamate. In one embodiment, an aliphatic amine may include 7 or more carbon atoms. In one embodiment, the amine used may include a heptyl amine, an octyl amine, and the like. In one embodiment, an amine may include an inorganic amine. A suitable inorganic amine may include one or more silicon atoms. A suitable inorganic amine may include one or more silicon-oxygen-silicon linkages. An organic or an inorganic amine may be obtained commercially or may be synthesized using appropriate reagents.

A method may include exposing the metal precursor to a stimulus. The stimulus may initiate a decomposition reaction of the metal precursor. The stimulus may include thermal energy or electromagnetic radiation. In one embodiment, the metal precursor may be heated to a decomposition temperature to initiate a decomposition reaction of the metal precursor. Decomposition temperature ranges may be as described herein above. In one embodiment, a decomposition reaction of the metal precursor may be initiated using laser irradiation. In one embodiment, the stimulus may include a reducing agent. A reducing agent may initiate a reduction of the metal cation to its elemental form. Decomposition and reduction of the metal precursor may result in formation of a metal nanoparticle and other decomposition products.

In one embodiment, decomposition and reduction conditions may such that the metal precursor may be converted to the elemental metal (or metal nanoparticle) relatively quickly. In one embodiment, about 50 percent of the metal in the metal precursor may be reduced to its elemental form in less than 1 minute, in less than about 5 minutes, in less than about 10 minutes, in less than about 20 minutes, in less than about 30 minutes, in less than about 45 minutes, or in less than about 60 minutes.

In one embodiment, decomposition and reduction conditions may such that after 45 minutes, yield of the metal nanoparticles may be in a range that is greater than about 40 percent, in a range that is greater than about 50 percent, in a range that is greater than about 60 percent, in a range that is greater than about 70 percent, or in a range that is greater than about 80 percent of the metal in the metal precursor.

In one embodiment, a metal nanoparticle may include a plurality of particles and two or more particles may be subjected to conditions resulting in formation of particle-particle bonds. In one embodiment, two or more nanoparticles may be heated to an appropriate sintering temperature to metallurgically-bond the metal nanoparticles. Sintering temperature ranges may be as described herein above.

In one embodiment, a secondary particle may be included in the composition. The method may include coating a surface of the secondary metal particle with a metal precursor prior to the decomposition reaction. The metal-precursor-coated secondary particle may be then exposed to a stimulus to form (plate-out) metal nanoparticles on the surface of the secondary particle. The particles may be then subjected to further heating to metallurgically-bond the metal nanoparticles and secondary metal particles.

In one embodiment, a metal precursor may be dispersed in a polymer precursor. Decomposition of the metal precursor in the polymer precursor may result in in-situ formation of metal nanoparticles. Dispersing of metal precursor in the polymer precursor may include mixing/blending in solid-form, melt form, or by solution mixing.

Solid- or melt blending of the polymer precursor and metal precursor may involve the use of one or more of shear force, extensional force, compressive force, ultrasonic energy, electromagnetic energy, or thermal energy. Blending may be conducted in a processing equipment wherein the aforementioned forces may be exerted by one or more of single screw, multiple screws, intermeshing co-rotating or counter rotating screws, non-intermeshing co-rotating or counter rotating screws, reciprocating screws, screws with pins, barrels with pins, rolls, rams, or helical rotors. The materials may by hand mixed but also may be mixed by mixing equipment such as dough mixers, chain can mixers, planetary mixers, twin screw extruder, two or three roll mill, Buss kneader, Henschel, helicones, Ross mixer, Banbury, roll mills, molding machines such as injection molding machines, vacuum forming machines, blow molding machine, or the like. Blending may be performed in batch, continuous, or semi-continuous mode. With a batch mode reaction, for instance, all of the reactant components may be combined and reacted until most of the reactants may be consumed. In order to proceed, the reaction has to be stopped and additional reactant added. With continuous conditions, the reaction does not have to be stopped in order to add more reactants. Solution blending may also use additional energy such as shear, compression, ultrasonic vibration, or the like to promote homogenization of the composition components. A polymer precursor and a metal precursor composition may also be contacted with a cure catalyst prior to blending or after blending.

In one embodiment, a dispersed composition may be prepared by solution blending of the polymer precursor and the metal precursor. In one embodiment, polymer precursor may be suspended in a fluid and then introduced into an ultrasonic sonicator along with the metal precursor to form a mixture. The mixture may be solution blended by sonication for a time period effective to disperse the metal precursor within the polymer precursor. In one embodiment, the fluid may swell the polymer precursor during the process of sonication. Swelling the polymer precursor may improve the ability of the metal precursor to impregnate the polymer precursor during the solution blending process and consequently improve dispersion.

Solvents may be used in the solution blending of the composition. A solvent may be used as a viscosity modifier, or to facilitate the dispersion and/or suspension of the metal precursor. Liquid aprotic polar solvents such as one or more of propylene carbonate, ethylene carbonate, butyrolactone, acetonitrile, benzonitrile, nitromethane, nitrobenzene, sulfolane, dimethylformamide, N-methylpyrrolidone, or the like may be used. Polar protic solvents such as one or more of water, methanol, acetonitrile, nitromethane, ethanol, propanol, isopropanol, butanol, or the like, may be used. Other non-polar solvents such as one or more of benzene, toluene, methylene chloride, carbon tetrachloride, hexane, diethyl ether, tetrahydrofuran, or the like, may also be used. Co-solvents comprising at least one aprotic polar solvent and at least one non-polar solvent may also be used. The solvent may be evaporated before, during and/or after the blending of the composition. After blending, the solvent may be removed by one or both of heating or of the application of vacuum. Removal of the solvent from the membrane may be measured and quantified by an analytical technique such as, infra-red spectroscopy, nuclear magnetic resonance spectroscopy, thermo gravimetric analysis, differential scanning calorimetric analysis, and the like.

A decomposition reaction of the metal precursor may be initiated to form a metal nanoparticle. In one embodiment, the polymer precursor may be subjected to reaction conditions to initiate curing during or after the decomposition reaction, resulting in a composition having a metal nanoparticle dispersed in a polymeric matrix. In certain embodiments where metal nanoparticles may be further metallurgically-bonded, the polymer precursor may be crosslinked after the metallurgical-bonding of the nanoparticles.

In one embodiment, a method of making a conductive feature is provided. The method may include disposing a metal precursor composition on a surface of a substrate. The metal precursor composition may include additives such as reducing agent, a solvent, a binder, a pigment, and the like. In one embodiment, the metal precursor composition may include a secondary metal particle, wherein the metal precursor is dispersed on a surface of the secondary metal particle. A metal precursor composition may be disposed by one or more of stencil printing, screen-printing, intaglio printing, gravure printing, lithographic printing, and flexographic printing.

In one embodiment, the metal precursor composition may be printed on a surface of a substrate by a direct write method such as ink-jet printing, an aerosol jet, or using an automated syringe. Ink-jet devices may operate by generating droplets of the composition and directing the droplets toward a surface. The position of the ink-jet head may be controlled and automated so that discrete patterns of the composition can be applied to the surface. During aerosol deposition, the composition may be aerosolized into droplets and the droplets may be transported to the substrate in a flow gas. The aerosol may be created using a number of atomization techniques such as ultrasonic atomization, two-fluid spray head, pressure atomizing nozzles, and the like. The metal precursor composition may be then immobilized on the substrate surface by heating or by laser patterning.

In one embodiment, a conductive adhesive composition may be disposed on the surface of a chip, on the surface of a wafer, or on the surface of a substrate. In certain embodiments, a conductive adhesive composition may include a metal precursor and a polymer precursor, wherein the metal precursor may be dispersed in the polymer precursor. In one embodiment, the conductive adhesive composition may not include a solvent and the composition may be solvent free. A suitable diluent may be added to facilitate processing of the conductive adhesive composition.

The conductive adhesive composition may be disposed on the surface in the form of one or more of bumps, balls, layers, lines, patterns, and the like. The conductive adhesive may be disposed using automated syringes or by any of the aforementioned printing methods.

In one embodiment, a conductive adhesive may be disposed on a surface of a substrate in the form of one set of bumps. A second set of bumps on a surface of second substrate (chip, wafer, and the like) may formed using the conductive adhesive. The two sets of bumps may be brought in contact with each other, aligned and pressed using an appropriate pressure. In one embodiment, a conductive adhesive may be heated to a decomposition temperature of the metal precursor. The decomposition temperature may be maintained for a required duration of time. Post decomposition, the electrically conductive adhesive may be heated to a sintering temperature of the metal nanoparticles. During or after the sintering of the metal nanoparticles, the conductive adhesive may be cured to form electrical interconnects.

In one embodiment, an underfill material may be disposed on the surface of the second substrate or between the first substrate and the second substrate along with the conductive adhesive. In one embodiment, the second substrate may be a chip and the chip may be flipped to align the first set of bumps with the second set of bumps. The flip-chip may be placed on the top of the substrate using an automatic pick and place machine. The placement force as well as the placement head dwell time may be controlled to optimize cycle time and yield of the process. The construction may be heated to form electrical interconnects and finally cure the underfill. The heating operation may be performed on the conveyor in the reflow oven.

By using one of the aforementioned methods, a chip may be packaged to form an electronic assembly. Chips that may be packaged using the conductive adhesive compositions may include semiconductor chips and LED chips. A suitable chip may include a semiconductor material, such as silicon, gallium, germanium or indium, or combinations of two or more thereof. The electronic assembly may be used in electronic devices, integrated circuits, semiconductor devices, and the like. Integrated circuits and other electronic devices employing the adhesive compositions described herein may be used in a wide variety of applications, including personal computers, control systems, telephone networks, and a host of other consumer and industrial products.

EXAMPLES

The following examples are intended only to illustrate methods and embodiments in accordance with the invention, and as such should not be construed as imposing limitations upon the claims. Unless specified otherwise, all ingredients may be commercially available from such common chemical suppliers as Alpha Aesar, Inc. (Ward Hill, Mass.), Sigma Aldrich, Spectrum Chemical Mfg. Corp. (Gardena, Calif.), and the like.

Example 1

Heptylamine (12.62 g, 1095 mol), heptane (200 mL), and 5 g of activated 4A molecular sieves are added to a round-bottomed flask. The mixture is stirred using a mechanical stirrer. Dry $CO_2$ (99.8%) is introduced in to the flask at a pressure of 7-8 psi (and vented through an oil bubbler) for about 45 minutes. Silver (I) oxide ($Ag_2O$, 0.219 mol) is added slowly to the reaction through the flask neck. The reaction is carried out for 12 hours after which, the flask is stoppered, and the reaction mixture is allowed to stir overnight. The reaction mixture is vacuum filtered and rinsed thoroughly with heptane. The solid filtrate is then collected for recrystallization and isolation. More particularly, the solid filtrate (5 g) is dispersed in 125 mL heptane, heated, and gravity filtered. The liquid filtrate is then cooled to room temperature and put in a freezer at −40° C. overnight. The liquid filtrate is removed from the freezer and vacuum filtered. The filtered solid is then transferred to a drying tube on high vacuum pump system to remove any remaining solvent and the (heptylcarbmato)silver (I) is collected.

Example 2

Octylamine (12.62 g, 1095 mol), heptane (200 mL), and 5 g of activated 4A molecular sieves are added to a round-bottomed flask. The mixture is stirred using a mechanical stirrer. Dry $CO_2$ (99.8%) is introduced in to the flask at a pressure of 7-8 psi (and vented through an oil bubbler) for about 45 minutes. Silver (I) oxide ($Ag_2O$, 0.219 mol) is added slowly to the reaction through the flask neck. The reaction is carried out for 12 hours after which, the flask is stoppered, and the reaction mixture is allowed to stir overnight. The reaction mixture is vacuum filtered and rinsed thoroughly with heptane. The solid filtrate is then collected for recrystallization and isolation. More particularly, the solid filtrate (5 g) is dispersed in 125 mL heptane, heated, and gravity filtered. The liquid filtrate is then cooled to room temperature and put in a freezer at −40° C. overnight. The liquid filtrate is removed from the freezer and vacuum filtered. The filtered solid is then transferred to a drying tube on high vacuum pump system to remove any remaining solvent and the (octylcarbmato)silver (I) is collected. Lower alkyl carbamate salts of silver are also synthesized by the procedure described herein above. The salts are highly hygroscopic and light sensitive and not used for further reactions. The details of different silver alkyl carbamates are described in Table 1.

Example 3

A silver carbamate with a siloxane ligand is synthesized according to the reaction procedure as described in FIG. 1. Trimethylsilyl chloride 10 is reacted with hexamethyl cyclotrisiloxane 20 to form a chloro-terminated linear siloxane 30. Chloro-terminated linear siloxane 30 is reacted with chlorodimethylsilane ethanol to form a hydrogen-terminated linear siloxane 40. Hydrogen-terminated linear siloxane 40 is reacted with a vinyl terminated silane in the presence of a Karstedt catalyst to form an amine-terminated linear siloxane 50. Amine-terminated linear siloxane 50 is reacted with carbon dioxide in the presence of a metal cation (silver oxide) to form silver precursor 60.

Example 4

Figure 2:
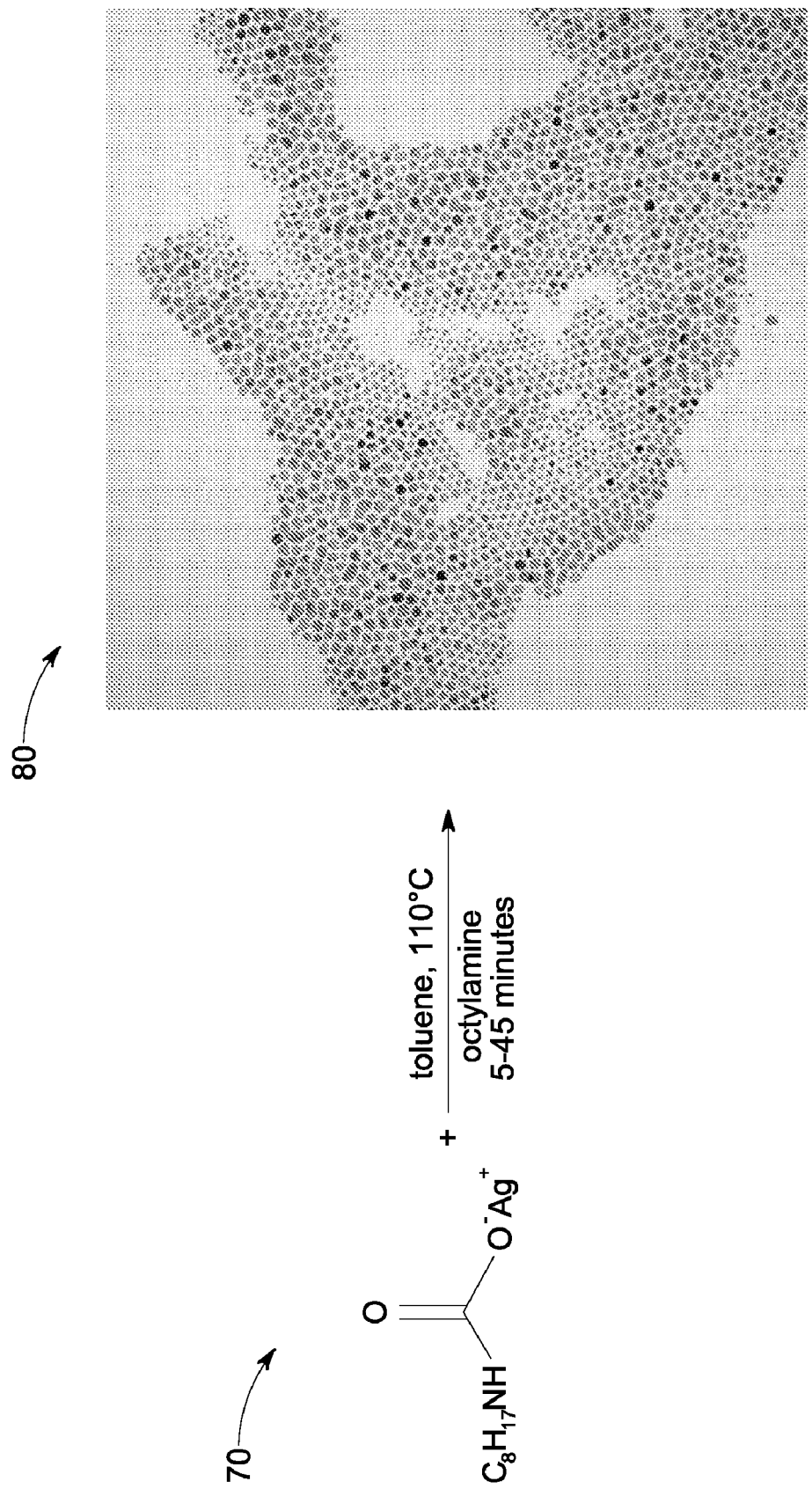
FIG. 2 is an illustration of a decomposition reaction of a metal precursor.

A silver salt synthesized in examples 1, 2, or 3 is used to form silver nanoparticles. In an exemplary embodiment, an (octylcarbamato)silver(I) (0.004 mol, 1.1285 g) salt 70, octylamine (0.002 mol, 0.2585 g), and toluene are added to a round-bottomed flask. The reaction mixture is stirred and the temperature of the reaction is increased slowly to a temperature of 110° C. The temperature of the reaction mixture is maintained at 110° C. for a fixed duration of time. Depending on the time duration for which the constant temperature was maintained, four different samples were collected, Samples 1, 2 3, and 4 corresponding to durations of 5 minutes, 10 minutes, 15 minutes, and 45 minutes respectively. After the required time period, the solution is cooled, and diluted with 42.5 mL of ethanol. The dilution solution is centrifuged at 13.9 krpm for 30 minutes at ~0° C., and decanted. Solids collected are washed with ethanol, recentrifuged as above, and decanted. Solids collected are washed with hexanes, centrifuged at 13.9 krpm for 20 minutes at ~10° C., and decanted. The solids are then dried under vacuum for 3 to 4 hours to remove any remaining solvents. Table 1 provides the percentage yield of nanoparticles formed using different metal precursors. Table 2 provides average particle size of samples 1, 2, 3 and 4. FIG. 2 is an illustration of silver nanoparticles 80 synthesized using (octylcarbamato)silver(I) and the synthesis procedure described hereinabove.

TABLE 1

Characteristics of silver alkyl carbamates

| Ag Carbamate | Yield | Stability | % Ag |
|---|---|---|---|
| Octyl- | 68 | dec. 90-95° C. | 38 |
| Heptyl- | 60 | dec. 90-95° C. | 41 |
| Hexyl- | — | Hygroscopic light sensitive | 43 |
| Pentyl- | — | Very hygroscopic light sensitive | 45 |
| Butyl- | — | Very hygroscopic light sensitive | 48 |

TABLE 2

Average particle size as function of time

| Sample No. | Time (min) | X ± s (nm) |
|---|---|---|
| 1 | 5 | 7.5 ± 2 |
| 2 | 10 | 9 ± 3 |
| 3 | 15 | 9 ± 4 |
| 4 | 45 | 11 ± 4 |

Example 5

Figure 3:
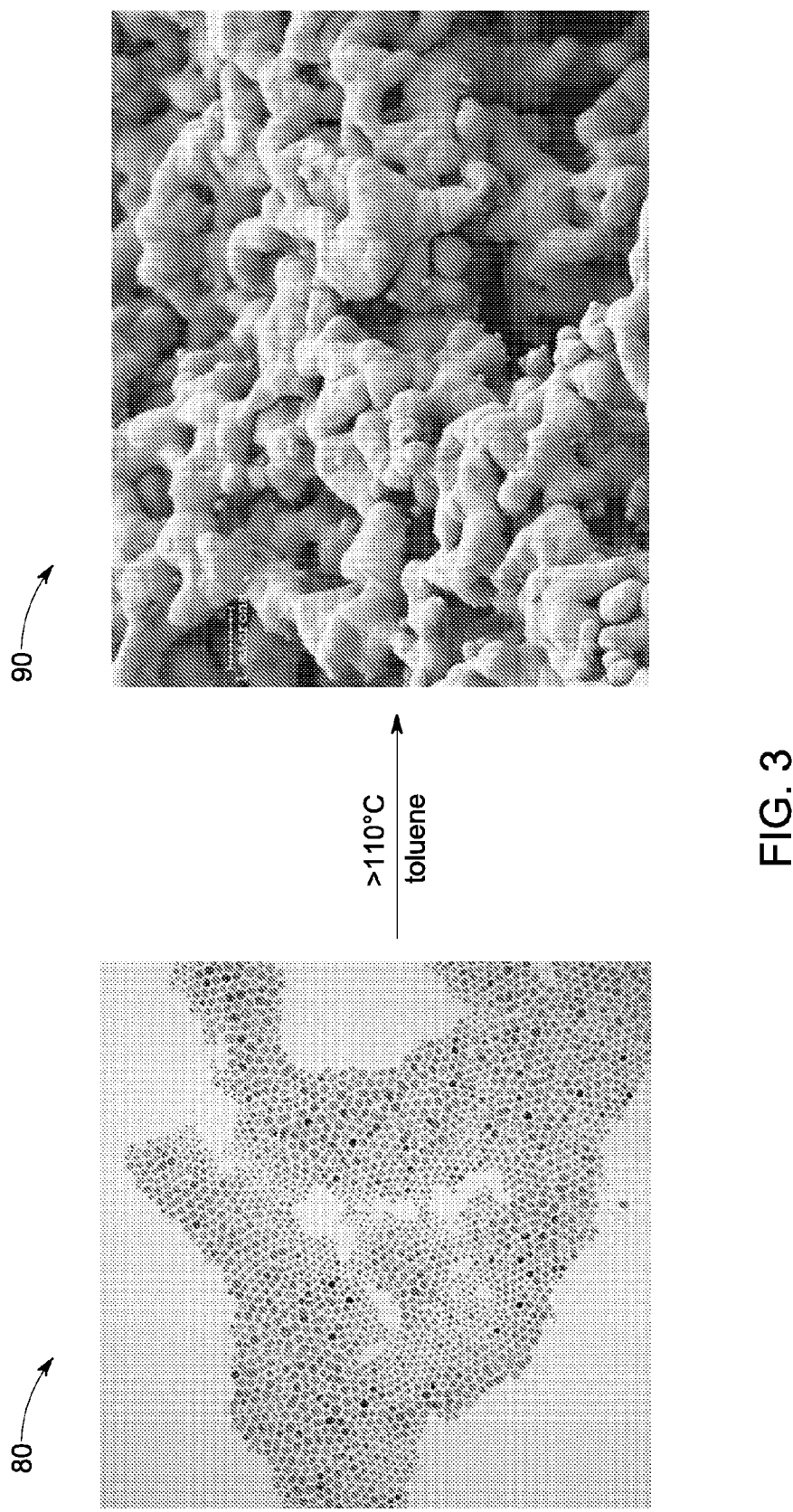
FIG. 3 is an illustration of metallurgical-bonding of a metal nanoparticle.

A solution of silver nanoparticles (synthesized in Example 4) in toluene is heated to a temperature greater than 110 degrees Celsius for a period of time. FIG. 3 shows the micrograph 90 of silver nanoparticles after being heated to a temperature greater than 110 degrees Celsius. The micrograph 90 shows the metallurgical bonding between the particles resulting in a continuous mass of metallurgically-bonded particles.

Example 6

Figure 4:
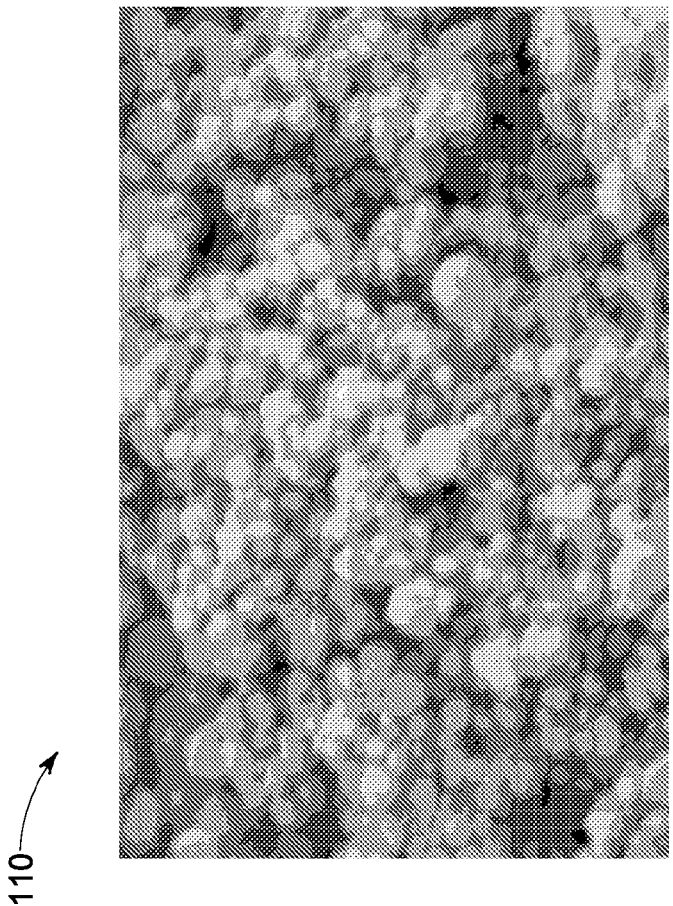
FIG. 4 is an illustration of a decomposition reaction and metallurgical-bonding of a metal precursor.
Figure 4:
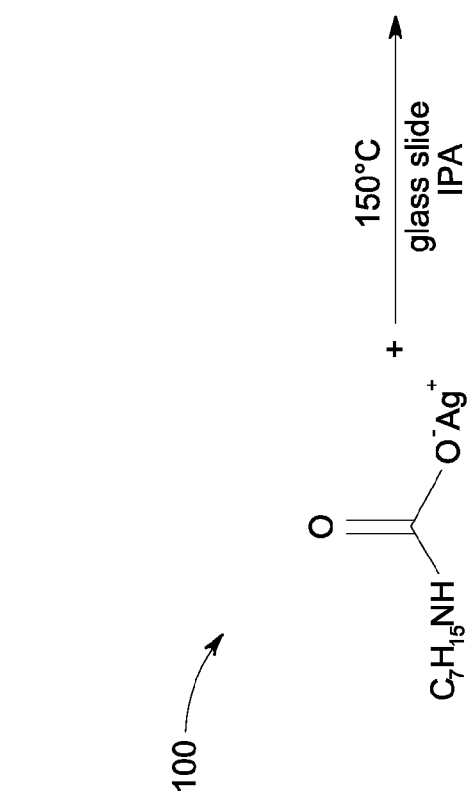

A solution of (heptylcarbamato)silver(I) 100 (synthesized in Example 1) in isopropanol (IPA) is heated to a temperature of 150 degrees Celsius for a period of time, resulting in one-step formation and metallurgical-bonding of silver nanoparticles. FIG. 4 shows the micrograph 110 of silver nanoparticles after being heated to a temperature of 150 degrees Celsius. The micrograph 110 shows the metallurgical bonding between the particles resulting in a continuous mass of metallurgically-bonded particles indicating that silver nanoparticles may have been synthesized as metastable intermediates prior to metallurgical bonding.

Example 6

Figure 6:
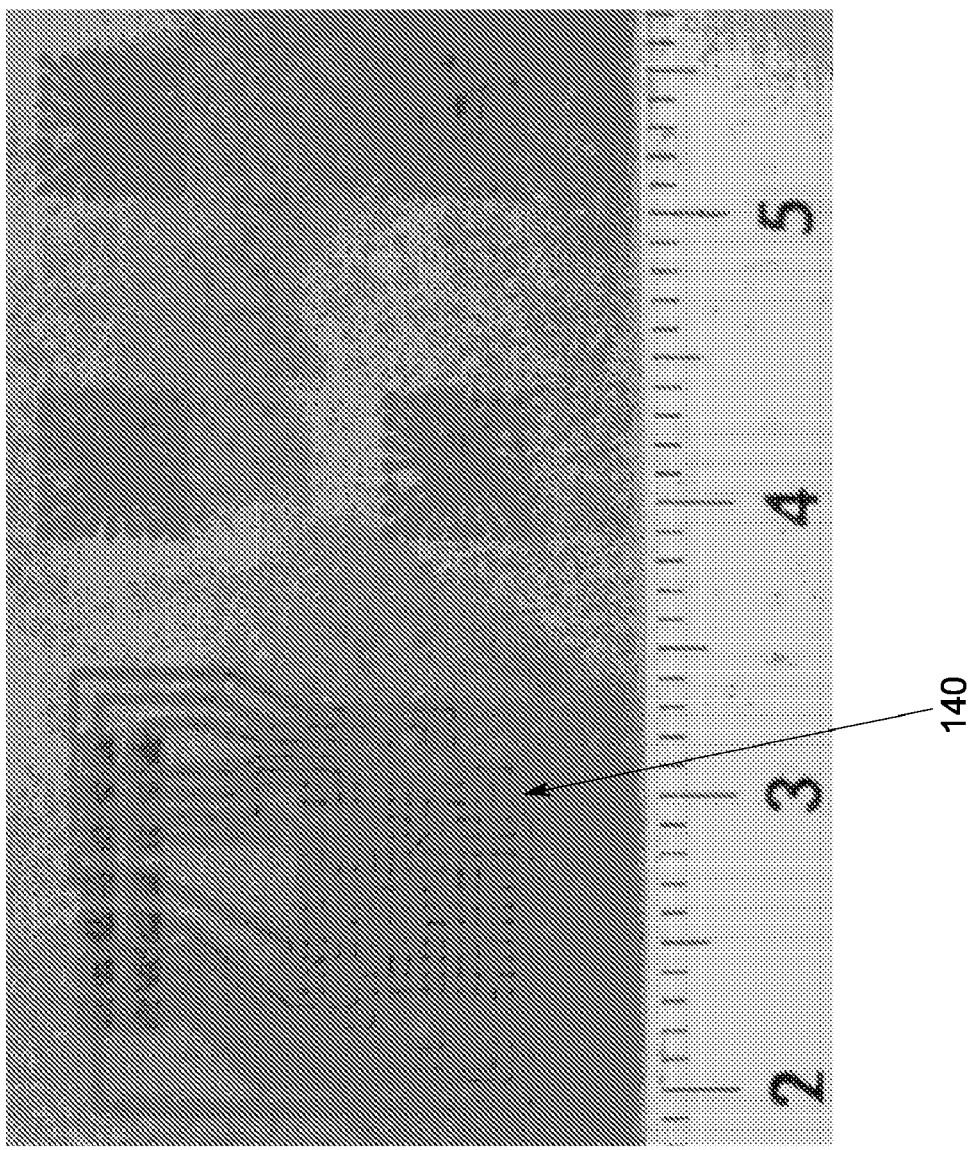
FIG. 6 is an image of a ball grid array patterned on a Kapton substrate using the metal precursor.

A solution of a metal precursor synthesized in Examples 1, 2, or 3 is printed on a Kapton sheet by stencil printing. The metal precursor solution is printed in the form of a ball grid array pattern 140 shown in FIG. 6. The printed solution may be heated to a suitable temperature (less than 110 degrees Celsius) to form silver nanoparticles and then heated to a temperature of 150 degrees Celsius to form metallurgical-bonding between particles. The printed solution may be heated directly to a temperature of 150 degrees Celsius to form nanoparticles and metallurgical-bonding between particles.

Example 7

Figure 7:
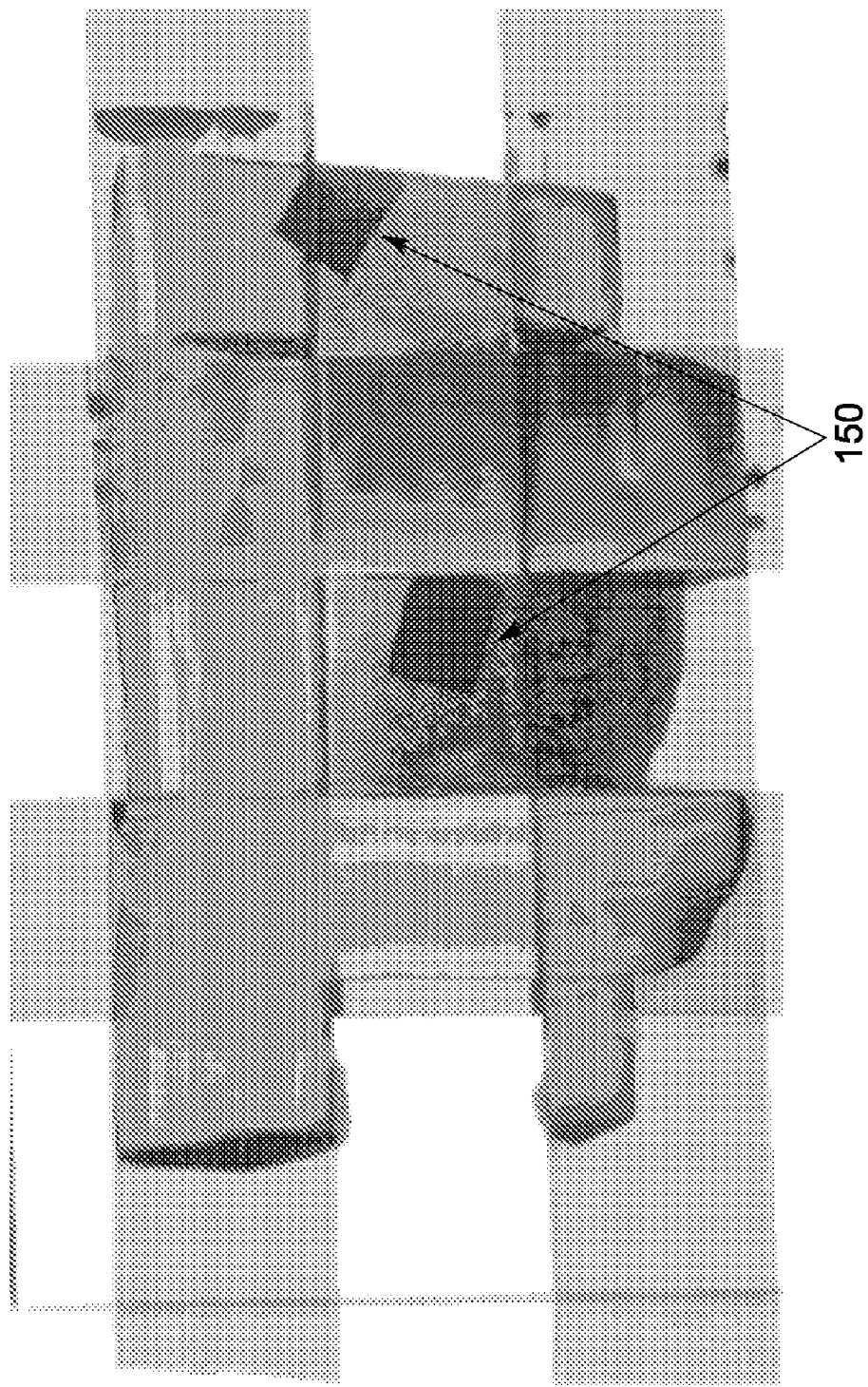
FIG. 7 is an image of laser patterns formed using the metal precursor.

A solution of a metal precursor synthesized in Examples 1, 2, or 3 and a thermochromic dye is coated on a glass slide. The solution is exposed to a laser beam (650 nm, 100 mA) to form patterns 150, shown in FIG. 7

Example 8

Figure 5:
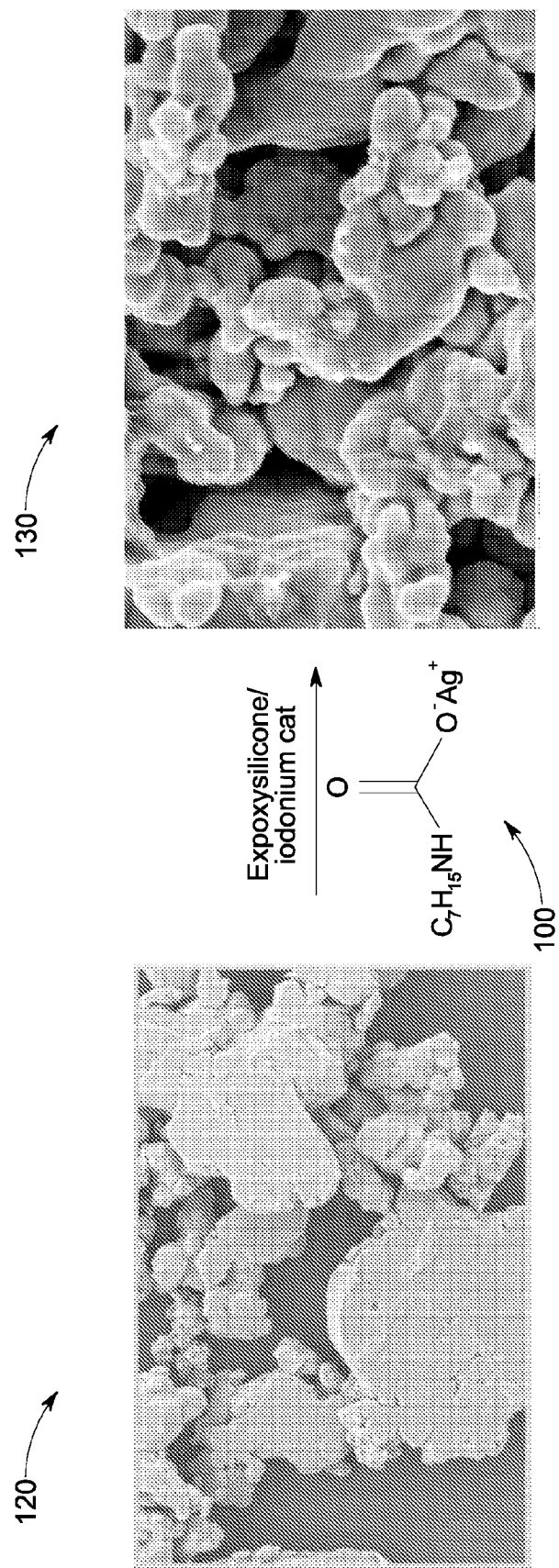
FIG. 5 is an illustration of metallurgical-bonding of metal nanoparticles with micron-sized particles in a polymer matrix.

An epoxy-functionalized polysiloxane (UV9400, $M^E D^E_{3.8} D_{94} M^E$) and iodonium catalyst (UV9392c) are obtained from GE Silicones. A (heptylcarbamato)silver(I) salt (synthesized in Example 1) is mixed with isopropanol to prepare a 1M solution. The resulting solution is filtered and stored in a vial. UV9400 (1 g), (heptylcarbamato)silver(I) salt/IPA (1.5 g), and silver flake (Ferro RDSF-101, 18.7 g) are measured into a plastic jar. The container is inserted into a FlackTec DAC 400 FV Speedmixer and spun at 1500 rpm for 10 seconds. The mixture is manually stirred and spun at 2100 rpm for an additional 10 seconds. UV9392c (0.0375 g) is measured into the plastic jar and the mixture is spun at 1500 rpm for 10 seconds. Material is manually stirred and spun at 2100 rpm for an additional 10 seconds. The resulting mixture is heated to a temperature of 150 degrees Celsius. FIG. 5 shows the micrographs of silver flakes 120 before the addition of the silver carbamate. The micrograph 130 shows the metallurgically-bonded silver particles after the addition of silver carbamate and heating to 150 degrees Celsius.

Example 9

An epoxy-functionalized polysiloxane (UV9400, $M^E D^E_{3.8} D_{94} M^E$) and iodonium catalyst (UV9392c) are obtained from GE Silicones. A (heptylcarbamato)silver(I) salt (synthesized in Example 1) is mixed with methacryloxypropyltrimethoxysilane (MAPTMS) to prepare a 1M solution. The resulting solution is filtered and stored in a vial. UV9400 (1 g), (heptylcarbamato)silver(I) salt/MAPTMS (1.5 g), and silver flake (Ferro RDSF-101, 18.7 g) are measured into a plastic jar. The container is inserted into a FlackTec DAC 400 FV Speedmixer and spun at 1500 rpm for 10 seconds. The mixture is manually stirred and spun at 2100 rpm for an additional 10 seconds. UV9392c (0.0375 g) is measured into the plastic jar and the mixture is spun at 1500 rpm for 10 seconds. Material is manually stirred and spun at 2100 rpm for an additional 10 seconds. The resulting mixture is heated to a temperature of 150 degrees Celsius for 1 hour. FIG. 5 shows the micrographs of silver flakes 120 before the addition of the silver carbamate. The micrograph 130 shows the metallurgically-bonded silver particles after the addition of silver carbamate and heating to 150 degrees Celsius.

Example 10

Figure 8:
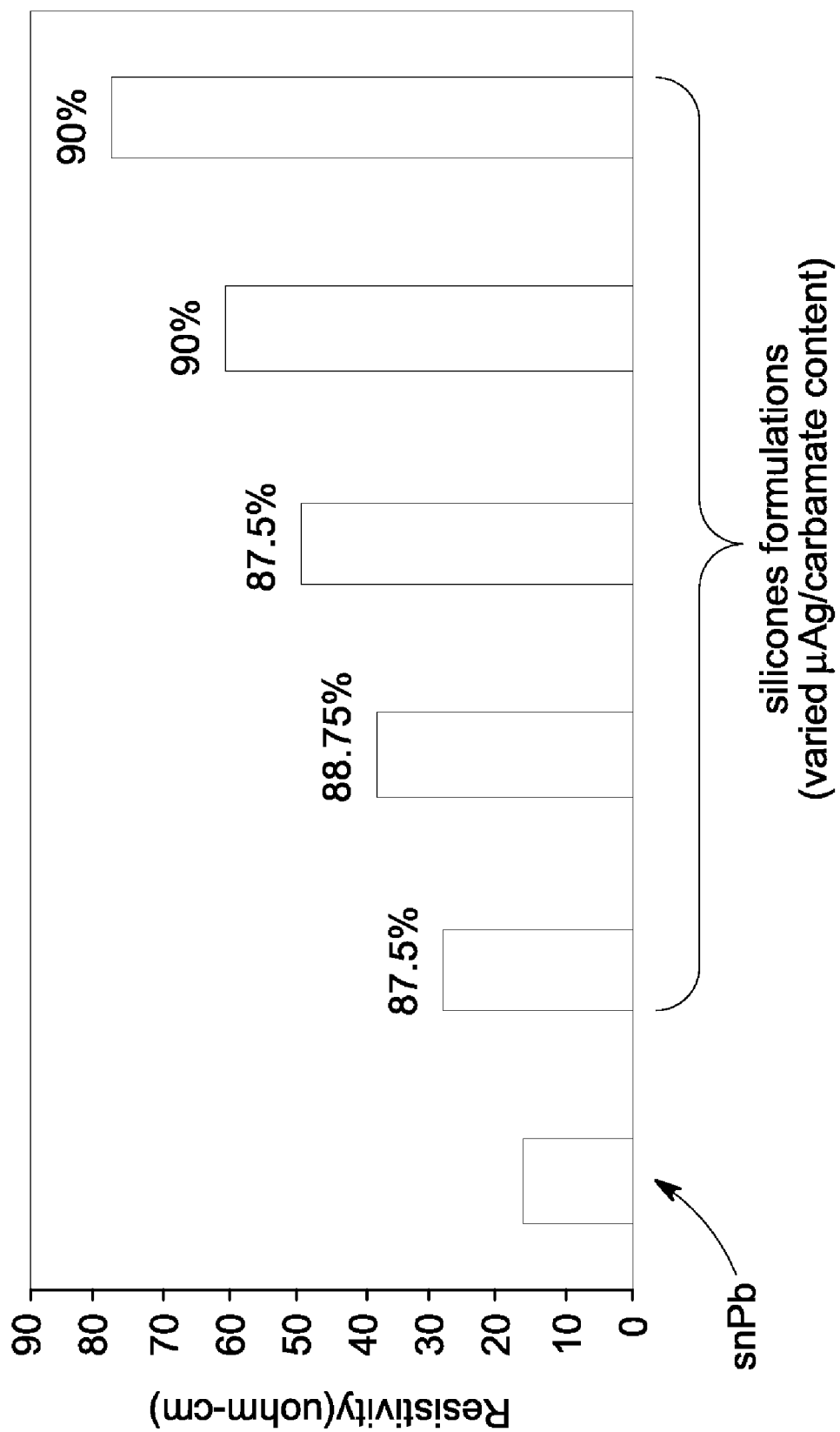
FIG. 8 is a bar chart of electrical resistivity for compositions according to embodiments of the invention.

Conductive adhesives are prepared according to procedure described hereinabove in Examples 8 and 9. Electrical resistivity values of different adhesives formulations are measured with varying silver carbamate content. FIG. 8 shows the electrical resistivity values for formulation with silver carbamates in comparison to a lead-tin solder using IPA as diluents (Example 8). A formulation with 87.5 percent silver carbamate content and in the presence of IPA shows an electrical resistivity value of 28 µOhm/centimeter, which is only 1.75 times greater than a lead-tin solder. A formulation with 87.5 percent silver carbamate content and in the presence of MAPTMS shows an electrical resistivity value of 24 µOhm/centimeter (not shown).

Example 11

Figure 9:
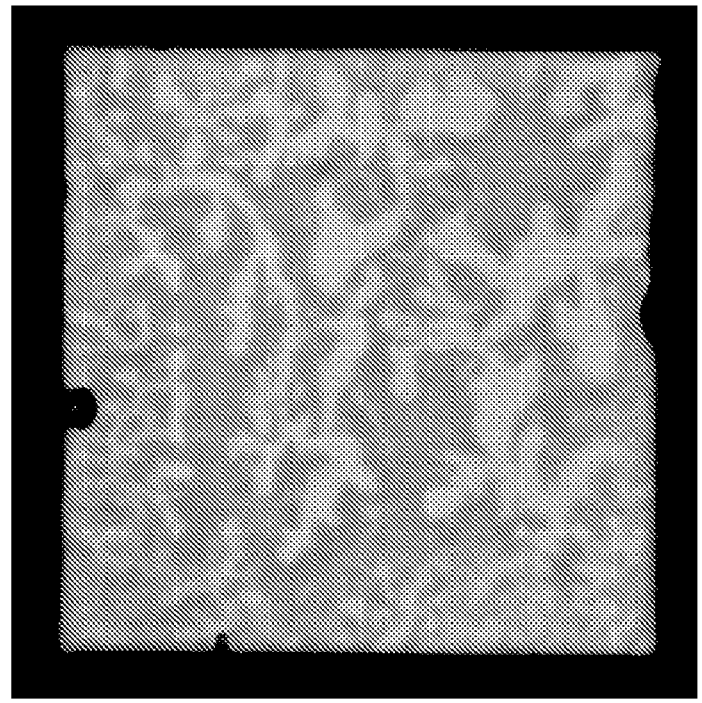
FIG. 9 is an image of a film formed using a metal precursor, a polymer matrix, and a solvent
Figure 10:
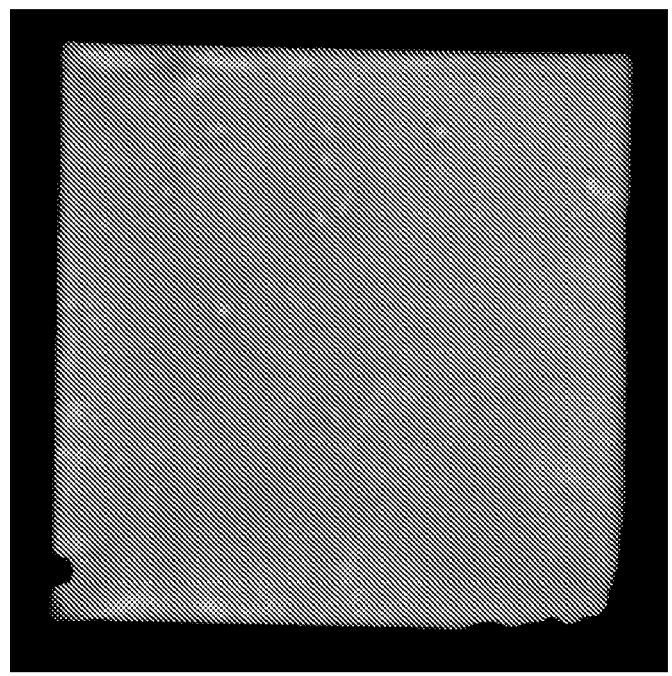
FIG. 10 is an image of a film formed using a metal precursor, a polymer matrix, and an inorganic diluent.

FIGS. 9 and 10 show images of films formed from formulation of Examples 8 and 9, after heating to a temperature of 160 degrees Celsius for duration of 1 hour. A film formed using IPA as diluent (FIG. 9) shows voids formation whereas a film formed using MAPTMS as diluent (FIG. 10) is relatively smooth. Absence of void formation may result in improved electrical performance of an adhesive formed using MAPTMS as a diluent.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

The foregoing examples are illustrative of some features of the invention. The appended claims are intended to claim the invention as broadly as has been conceived and the examples herein presented are illustrative of selected embodiments from a manifold of all possible embodiments. Accordingly, it is Applicants' intention that the appended claims not be limited to the illustrated features of the invention by the choice of examples utilized. As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges there between. It is to be expected that variations in these ranges will suggest themselves to a practitioner having ordinary skill in the art and, where not already dedicated to the public, the appended claims should cover those variations. Advances in science and technology may make equivalents and substitutions possible that are not now contemplated by reason of the imprecision of language; these variations should be covered by the appended claims.

The invention claimed is:

1. A nanoparticle forming composition, comprising:
a metal precursor comprising an inorganic ligand and a metal cation, wherein the inorganic ligand comprises silicon and a carbamate group and the metal precursor comprises a structure of formula (I)

$$R^1-HN-\overset{\overset{O}{\|}}{C}-O^-X^{+n} \quad (I)$$

wherein "n" is 1 or 2, $X^+$ is the metal cation, and $R^1$ comprises a structure of formula (II):

$$M_aD_bT_cQ_dR^2 \quad (II)$$

wherein the subscripts "a", "b", "c", and "d" are independently zero or a positive integer, and the sum of integers "a", "b", "c", and "d" is greater than or equal to 1, and M has the formula:

$$R^3R^4R^5SiO_{1/2}, \quad (III)$$

D has the formula:

$$R^6R^7SiO_{2/2}, \quad (IV)$$

T has the formula:

$$R^8SiO_{3/2}, \quad (V)$$

and Q has the formula:

$$SiO_{4/2}, \quad (VI)$$

and $R^2$ is a divalent aliphatic radical having formula $$(-Si(R^9)(R^{10})-CH_2-CH(R^{11})(R^{12})_z-,$$

wherein $R^3$ to $R^{10}$ are independently an aliphatic radical, a cycloaliphatic radical, or an aromatic radical; $R^{11}$ is a hydrogen atom or an aliphatic radical; $R^{12}$ is a divalent aliphatic radical, and "z" is 0 or 1; and
wherein the metal precursor responds to electromagnetic or thermal stimulus to form a metal nanoparticle.

2. The nanoparticle forming composition as defined in claim 1, wherein $R^1$ comprises a structure of formula (IX):

$$MD_bR^2 \quad (IX)$$

wherein "b" is an integer greater than or equal to 0, M has the formula:

$$R^3R^4R^5SiO_{1/2}, \quad (III)$$

D has the formula:

$$R^6R^7SiO_{2/2}, \quad (IV)$$

and $R^2$ is a divalent aliphatic radical having formula $$-Si(R^9)(R^{10})-CH_2-CH(R^{11})(R^{12})_z-, \quad (VIII)$$

wherein $R^3$ to $R^{10}$ are independently an aliphatic radical, a cycloaliphatic radical, or an aromatic radical, $R^{11}$ is a hydrogen atom or an aliphatic radical, $R^{12}$ is a divalent aliphatic radical, and "z" is 0 or 1.

3. The nanoparticle forming composition as defined in claim 1, wherein the metal cation is a silver cation.

4. The nanoparticle forming composition as defined in claim 1, wherein the metal precursor responds to thermal stimulus.

5. The nanoparticle forming composition as defined in claim 4, wherein the thermal stimulus is insufficient to heat the composition to a temperature that is greater than about 120 degrees Celsius.

6. The nanoparticle forming composition as defined in claim 5, wherein the inorganic ligand decomposes in response to the thermal stimulus to form an amine.

7. The nanoparticle forming composition as defined in claim 6, wherein the amine stabilizes the surface of the metal nanoparticle.

8. The nanoparticle forming composition as defined in claim 1, wherein the metal precursor responds to electromagnetic stimulus.

9. The nanoparticle forming composition as defined in claim 8, wherein the electromagnetic stimulus comprises ultraviolet radiation.

10. The nanoparticle forming composition as defined in claim 1, further comprising:
additional metal precursors, each comprising an inorganic ligand and a metal cation, wherein the inorganic ligand comprises a carbamate group.

11. The nanoparticle forming composition of claim 10, wherein the additional metal precursors comprise different inorganic ligands.

12. The nanoparticle forming composition of claim 10, wherein the additional metal precursors comprises the same inorganic ligand.

13. The nanoparticle forming composition as defined in claim 1, further comprising a secondary metal particle.

14. The nanoparticle forming composition of claim 13, wherein the secondary metal particle comprises copper, silver, platinum, palladium, gold, tin, indium, aluminum, or a combination thereof.

15. The nanoparticle forming composition of claim 13, wherein the metal precursor is operatively disposed relative to a surface of the secondary metal particle.

16. The nanoparticle forming composition of claim 13, further comprising a filler material.

17. The nanoparticle forming composition of claim 16, wherein the filler material is electrically conductive.

18. The nanoparticle forming composition of claim 16, wherein the filler material is thermally conductive.

19. The nanoparticle forming composition of claim 16, wherein the filler material comprises silica.

20. The nanoparticle forming composition of claim 19, wherein the filler material comprises colloidal silica.

* * * * *

UNITED STATES PATENT AND TRADEMARK OFFICE
CERTIFICATE OF CORRECTION

PATENT NO. : 7,632,425 B1
APPLICATION NO. : 11/539330
DATED : December 15, 2009
INVENTOR(S) : Simone et al.

It is certified that error appears in the above-identified patent and that said Letters Patent is hereby corrected as shown below:

On the Title Page, in Field (75), under "Inventors:", in Column 1, Line 5, delete "Gulfort" and insert -- Gulfport --, therefor.

On the Title Page, in Field (56), under "U.S. PATENT DOCUMENTS", in Column 2, Line 16, delete "2005/0008861 A1  1/2005  Yadav et al." and insert -- 2005/0008861 A1*  1/2005  Yadav et al.  428-/403 --, therefor.

Title Page 2, in Field (56), under "OTHER PUBLICATIONS", in Column 1, Line 1, delete "d" and insert -- d^10 --, therefor.

Title Page 2, in Field (56), under "OTHER PUBLICATIONS", in Column 2, Line 34, delete "TUnable" and insert -- Tunable --, therefor.

In Column 2, Line 27, delete "solvent" and insert -- solvent. --, therefor.

In Column 6, Line 58, before ""b"", insert -- wherein --.

In Column 7, Line 67, delete "by" and insert -- be --, therefor.

In Column 8, Line 55, delete "anine." and insert -- amine. --, therefor.

In Column 24, Line 1, delete "Theological" and insert -- rheological --, therefor.

In Column 26, Line 14, delete "Theological" and insert -- rheological --, therefor.

In Column 34, Line 58, delete "Example 6" and insert -- Example 7 --, therefor.

In Column 35, Line 5, delete "Example 7" and insert -- Example 8 --, therefor.

In Column 35, Line 12, delete "Example 8" and insert -- Example 9 --, therefor.

Signed and Sealed this

Eighth Day of June, 2010

David J. Kappos
*Director of the United States Patent and Trademark Office*

In Column 35, Line 34, delete "Example 9" and insert -- Example 10 --, therefor.

In Column 35, Line 58, delete "Example 10" and insert -- Example 11 --, therefor.

In Column 36, Line 7, delete "Example 11" and insert -- Example 12 --, therefor.

UNITED STATES PATENT AND TRADEMARK OFFICE
CERTIFICATE OF CORRECTION

PATENT NO.       : 7,632,425 B1
APPLICATION NO.  : 11/539330
DATED            : December 15, 2009
INVENTOR(S)      : Simone et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this

Second Day of November, 2010

David J. Kappos
*Director of the United States Patent and Trademark Office*